(12) United States Patent
Boyer et al.

(10) Patent No.: US 7,807,383 B2
(45) Date of Patent: Oct. 5, 2010

(54) DIAGNOSING AND TREATING HORMONE RESISTANT CANCERS

(75) Inventors: Thomas G. Boyer, San Antonio, TX (US); Amy M. Trauernicht, Chula Vista, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/104,709

(22) Filed: Apr. 17, 2008

(65) Prior Publication Data

US 2009/0062179 A1    Mar. 5, 2009

Related U.S. Application Data

(60) Provisional application No. 60/912,752, filed on Apr. 19, 2007.

(51) Int. Cl.
  G01N 33/48    (2006.01)
  G01N 33/53    (2006.01)
  G01N 33/567   (2006.01)

(52) U.S. Cl. .......................... 435/7.1; 435/7.8; 436/63; 436/64; 436/503; 436/811

(58) Field of Classification Search .................. None
See application file for complete search history.

(56) References Cited

OTHER PUBLICATIONS

Tolcher et al (Clinical Cancer Research, 2002, vol. 8, pp. 2530-2535).*
Cripps et al (Clinical Cancer Research. 2002, 8, pp. 2188-2192).*
James and Gibson (Blood, 1998, vol. 91, pp. 371-382).*
Extended Medline abstract of Mangala et al, Methods in Mol. Biol 2009.*
Extended Medline abstract of Koldenhoff et al, Methods in Mol Bio, 2009.*
Merkel et al, Mol Pharmaceutics, 2009, vol. 8, pp. 1246-1280.*
Song et al, Exp Mol Med, 2007, vol. 39, pp. 722-732.*
Difeo et al, Cancer Research, 2009, vol. 69, pp. 4733-4741.*
He et al, Cancer biotherapy and Radiopharm, 2009, vol. 24, pp. 249-259.*
Jain (Science, 1996, vol. 271, pp. 1079-1080).*
Taratula et al, Journal of controlled Release, 2009, vol. 140, pp. 284-293.*
Ali and Coombes. 2000. Estrogen receptor alpha in human breast cancer: occurrence and significance. J Mammary Gland Biol Neoplasia 5:271-81.
Bagatell et al. 2001. Destabilization of steroid receptors by heat shock protein 90-binding drugs: a ligand-independent approach to hormonal therapy of breast cancer. Clin Cancer Res 7:2076-84.
Beausoleil et al. 2004. Large-scale characterization of HeLa cell nuclear phosphoproteins. Proc. Natl Acad Sci U S A 101: 12130-5.
Bhat-Nakshatri et al. 2002. Identification of signal transduction pathways involved in constitutive NF-kappaB activation in breast cancer cells. Oncogene 21:2066-78.
Bittner. 2005. A window on the dynamics of biological switches. Nat Biotechnol 23:183-4.
Bouker et al. 2004. Interferon regulatory factor-1 mediates the proapoptotic but not cell cycle arrest effects of the steroidal antiestrogen ICI 182,780 (faslodex, fulvestrant). Cancer Res. 64:4030-9.
Bouwmeester et al. 2004. A physical and functional map of the human TNF-alpha/NF-kappa B signal transduction pathway. Nat Cell Biol 6:97-105.
Brunner et al. 1997. MCF7/LCC9: an antiestrogen-resistant MCF-7 variant in which acquired resistance to the steroidal antiestrogen ICI 182,780 confers an early cross-resistance to the nonsteroidal antiestrogen tamoxifen. Cancer Res. 57:3486-93.
Clarke et al. 2004. Steroid receptors in human breast cancer. Trends Endocrinol Metab 15:316-23.
Clarke et al. 1989. Progression of human breast cancer cells from hormone-dependent to hormone-independent growth both in vitro and in vivo. Proc Natl Acad Sci U S A 86:3649-53.
Colditz et al. 2004. Risk factors for breast cancer according to estrogen and progesterone receptor status. J Natl Cancer Inst 96:218-28.
Couse and Korach. 1999. Estrogen receptor null mice: what have we learned and where will they lead us? Endocr Rev 20:358-417.
deGraffenried et al. 2004. NF-kappa B inhibition markedly enhances sensitivity of resistant breast cancer tumor cells to tamoxifen. Ann Oncol 15:885-90.
Dowsett et al. 1999. Clinical studies of apoptosis and proliferation in breast cancer. Endocr Relat Cancer 6:25-8.
Fanelli et al. 1996. Estrogen receptors, progesterone receptors, and cell proliferation in human breast cancer. Breast Cancer Res Treat 37:217-28.
Fliss et al. 2000. Control of estrogen receptor ligand binding by Hsp90. J Steroid Biochem Mol Biol 72:223-30.
Hamaguchi et al. 2002. DBC2, a candidate for a tumor suppressor gene involved in breast cancer. Proc Natl Acad Sci U S A 99:13647-52.
Hilakivi-Clarke et al. 2002. Dietary modulation of pregnancy estrogen levels and breast cancer risk among female rat offspring. Clin Cancer Res 8:3601-10.
Howell. 2006. Pure oestrogen antagonists for the treatment of advanced breast cancer. Endocr Relat Cancer 13:689-706.
Huang et al. 2005. Molecular basis of therapeutic strategies for breast cancer. Curr Drug Targets Immune Endocr Metabol Disord 5:379-96.
Ignar-Trowbridge et al. 1993. Peptide growth factors elicit estrogen receptor-dependent transcriptional activation of an estrogen-responsive element. Mol Endocrinol 7:992-8.
Jordan. 2004. Selective estrogen receptor modulation: concept and consequences in cancer. Cancer Cell 5:207-13.
Key et al. 2001. Epidemiology of breast cancer. Lancet Oncol 2:133-40.
Koibuchi et al. 1999. The mechanisms of antitumor effects of luteinizing hormone releasing hormone agonist (buserelin) in 7, 12-dimethylbenz(a)anthracene-induced rat mammary cancer. Int J Mol Med 4:145-8.
Lee et al. 2002. Radicicol represses the transcriptional function of the estrogen receptor by suppressing the stabilization of the receptor by heat shock protein 90. Mol Cell Endocrinol 188:47-54.
Liao et al. 1998. Promotion of estrogen-induced mammary gland carcinogenesis by androgen in the male Noble rat: probable mediation by steroid receptors. Carcinogenesis 19:2173-80.
Liu and Picard. 1998. Bioactive steroids as contaminants of the common carbon source galactose. FEMS Microbiol Lett 159:167-71.

(Continued)

Primary Examiner—Karen A Canella
(74) Attorney, Agent, or Firm—Fish & Richardson P.C.

(57) ABSTRACT

Provided herein are methods and compositions related to diagnosing and treating hormone resistant cancers.

7 Claims, 10 Drawing Sheets

OTHER PUBLICATIONS

Mandlekar and Kong. 2001. Mechanisms of tamoxifen-induced apoptosis. Apoptosis 6:469-77.

McDonnell and Norris. 2002. Connections and regulation of the human estrogen receptor. Science 296:1642-4.

Nakshatri et al. 1997. Constitutive activation of NF-kappaB during progression of breast cancer to hormone independent growth. Mol Cell Biol 17:3629-39.

Nilsson et al. 2001. Mechanisms of estrogen action. Physiol Rev 81:1535-65.

Normanno et al. 2005. Mechanisms of endocrine resistance and novel therapeutic strategies in breast cancer. Endocr Relat Cancer 12:721-47.

Osborne and Schiff. 2005. Estrogen-receptor biology: continuing progress and therapeutic implications. J Clin Oncol 23:1616-22.

Pratt et al. 2003 Estrogen withdrawal-induced NF-kappaB activity and bcl-3 expression in breast cancer cells: roles in growth and hormone independence. Mol Cell Biol 23:6887-900.

Pratt and Toft. 1997. Steroid receptor interactions with heat shock protein and immunophilin chaperones. Endocr Rev 18:306-60.

Qi et al. 2002. Identification of protein arginine methyltransferase 2 as a coactivator for estrogen receptor alpha. J Biol Chem 277:28624-30.

Radvanyi et al. 2005. The gene associated with trichorhinophalangeal syndrome in humans is overexpressed in breast cancer. Proc Natl Acad Sci U S A 102:11005-10.

Rau et al. 2005. The mechanisms and managements of hormone-therapy resistance in breast and prostate cancers. Endocr Relat Cancer 12:511-32.

Reid et al. 2003. Cyclic, proteasome-mediated turnover of unliganded and liganded ERalpha on responsive promoters is an integral feature of estrogen signaling. Mol Cell 11:695-707.

Richardson et al. 2006. X chromosomal abnormalities in basal-like human breast cancer. Cancer Cell 9:121-32.

Riggins et al. 2005. Antiestrogens, aromatase inhibitors, and apoptosis in breast cancer. Vitam Horm 71:201-37.

Schiff et al. 2004. Cross-talk between estrogen receptor and growth factor pathways as a molecular target for overcoming endocrine resistance. Clin Cancer Res 10:331S-6S.

Sommer and Fuqua. 2001. Estrogen receptor and breast cancer. Semin Cancer Biol 11:339-52.

Sundararajan et al. 2005. Caspase-dependent processing activates the proapoptotic activity of deleted in breast cancer-1 during tumor necrosis factor alpha-mediated death signaling. Oncogene 24:4908-20.

Trauernicht and Boyer. 2006. Modulation of estrogen receptor alpha (ER) expression and function by the product of the deleted in breast cancer 1 (DBC-1) gene. Regulation of Eukaryotic Transcription: From Chromatin to mRNA. Keystone Symposia, Taos, New Mexico.

Trauernicht et al. 2007. Modulation of estrogen receptor alpha protein level and survival function by DBC-1. Mol. Endocrinol. 21:1526-36.

Turner and Weintraub. 1994. Expression of achaete-scute homolog 3 in Xenopus embryos converts ectodermal cells to a neural fate. Genes Dev 8:1434-47.

van de Vijver et al. 2002. A gene-expression signature as a predictor of survival in breast cancer. N Engl J Med 347:1999-2009.

Zhao et al. 2004. Different gene expression patterns in invasive lobular and ductal carcinomas of the breast. Mol Biol Cell 15:2523-36.

Zheng et al. 2001. BRCA1 mediates ligand independent transcriptional repression of the estrogen receptor. Proc Natl Acad Sci U S A 98:9587-92.

Zhou et al. 2005. Activation of nuclear factor-kappaB (NFkappaB) identifies a high-risk subset of hormone dependent breast cancers. Int J Biochem Cell Biol 37:1130-44.

Zhou et al. 2005. The NFkappaB pathway and endocrine-resistant breast cancer. Endocr Relat Cancer 12 Suppl 1:S37-46.

* cited by examiner

DIAGNOSING AND TREATING HORMONE RESISTANT CANCERS

CROSS-REFERENCE TO RELATED APPLICATIONS

This application claims priority to U.S. Provisional Application No. 60/912,752, filed Apr. 19, 2007, which is incorporated by reference herein in its entirety.

STATEMENT REGARDING FEDERALLY FUNDED RESEARCH

This invention was funded by the National Institutes of Health (Grant Nos. 5T32CA086800-04 and CA098301-01) and the U.S. Army Department of Defense (Grant No. DAMD17-02-1-0584). The government has certain rights in this invention.

BACKGROUND

The response of receptors to hormones is particularly important in the development of a number of diseases, including cancer. Hormone resistant cancers include certain breast, endometrial, ovarian and prostate cancers.

Breast cancer is the leading cause of death among American women between the ages of 20 and 59. Among a variety of established etiological factors linked to breast cancer, the steroid hormone estrogen (17-β-estradiol; E2) has long been implicated in disease pathogenesis. Numerous animal studies have revealed that E2 can induce and promote breast cancer, while estrogen ablation therapy or the administration of anti-estrogens can oppose these effects. The physiological effects of E2 in the breast are mediated by cognate receptors that are expressed as two structurally related subtypes, estrogen receptor α (ERα) and β (ERβ). ERα is the predominant receptor isoform expressed in breast cancer cells, and approximately 70% of breast cancer patients score positive for ERα at diagnosis. ERα is therefore a predictive factor with respect to breast cancer development and hormone sensitivity status. Endocrine therapy, which seeks to block ER-mediated mitogenic signaling, has emerged as one of the most important systemic therapies in breast cancer management. However, therapeutic resistance, either inherent (de novo resistance) or acquired during treatment (acquired resistance) remains a significant clinical roadblock to effective disease management.

Prostate cancer is the second leading cause of cancer death among males in the United States. Although survival rates are good for prostate cancer that is diagnosed early, the treatments for advanced disease are limited to hormone ablation techniques and palliative care. Hormone ablation techniques (orchiectomy and anti-androgen treatments) generally allow only temporary remission of the disease. It usually recurs within 1-3 years of treatment, with the recurrent tumors no longer requiring androgens for growth and survival. Therapy with conventional chemotherapeutic agents, such as progesterone, estramustine and vinblastine, has also not been demonstrated to be effective to halt progression of the disease.

SUMMARY

Provided herein are methods and compositions related to diagnosing and treating hormone resistant cancers. Specifically, provided is a method of determining whether a cancer cell is sensitive to endocrine therapy by determining the level of expression or activity of Deleted in Breast Cancer-1 (DBC-1) or the presence of binding of DBC-1 and Estrogen Receptor α (ERα) in the cell. Also provided is a method of determining whether a subject with cancer is suitable for treatment with endocrine therapy comprising determining the level of expression or activity of DBC-1 or the presence of binding of DBC-1 and ERα.

Provided is a method of determining a susceptibility to hormone resistant cancer in a subject comprising determining the level of expression or activity of DBC-1 or the presence of binding of DBC-1 and ERα. Also provided is a method of inducing apoptosis of cancer cells comprising selecting a population of hormone resistant cancer cells and contacting the hormone resistant cancer cells with an agent that inhibits expression of DBC-1 or binding of DBC-1/ERα.

Provided is a method of treating hormone resistant cancer in a subject, comprising selecting a subject with hormone resistant cancer and administering an agent that inhibits expression of DBC-1 or binding of DBC-1/ERα to the subject.

The details of one or more embodiments are set forth in the accompanying drawings and the description below. Other features, objects, and advantages will be apparent from the description and drawings, and from the claims.

BRIEF DESCRIPTION OF DRAWINGS

FIG. 1A shows mammalian two-hybrid interaction analysis. HeLa cells cultured in hormone-free medium for three days were transfected with the indicated combinations of mammalian expression plasmids encoding the yeast GAL4 DNA-binding domain (GAL4), the Herpes simplex virus VP16 transactivation domain (VP16), a GAL4-DBC-1 chimera, and a VP16-ERα chimera. Twenty-four hours post-transfection cells were treated without (−E2) or with (+E2) 17-β-estradiol ($10^{-7}$ M) for an additional twenty-four hours prior to cell harvest and assay of transfected whole cell lysates for luciferase activity produced from a co-transfected GAL4 DNA-binding site driven-reporter template. Luciferase values are expressed relative to the luciferase activity obtained in cells transfected with both the GAL4 and VP16 expression vectors, which was arbitrarily assigned a value of 1. Luciferase activities were first normalized to β-galactosidase activity obtained by cotransfection of a β-galactosidase expression vector. Error bars represent the standard deviation (S.D.) from the average of at least three independent transfections performed in duplicate. Note that estrogen abolishes the interaction between GAL4-DBC-1 and VP16-ERα. FIG. 1B shows mammalian two-hybrid interaction analysis. For FIG. 1B, top panel, HeLa cells cultured for three days in hormone-free medium (−E2) were transfected with the indicated combinations of mammalian expression plasmids encoding GAL4, VP16, a GAL4-DBC-1-N terminal chimera (amino acids 1-478), a GAL4-DBC-1-C terminal chimera (amino acids 479-923), and a VP16-ERα chimera. Forty-eight hours post-transfection, cells were harvested and transfected whole cell lysates were assayed for luciferase activity produced from a cotransfected GAL4 DNA-binding site driven-reporter template as described in FIG. 1A. Note that ERα interacts exclusively with the N-terminus of DBC-1. For FIG. 1B, bottom panel, harvested whole cell lysates were resolved by SDS-12%-PAGE and processed by immunoblot analysis with antibodies specific for GAL4-DBD or ERα as indicated by arrows. Note that differences in the relative expression levels of the GAL4-DBC-1 chimerae cannot explain differences in their respective ERα-binding capabilities. Results are representative of at least three independent experiments.

FIGS. 1C and 1D show co-immunoprecipitation analysis. For FIG. 1C MCF-7 cells cultured in hormone-free medium for three days were treated without (−E2) or with (+E2) 17-β-estradiol ($10^{-7}$ M) for one hour prior to cell harvest and immunoprecipitation of whole cell lysates with antibodies specific for ERα (top panel) or DBC-1 (bottom panel). Immunoprecipitates were resolved by SDS-10%-PAGE and processed by immunoblot analysis using antibodies specific for DBC-1 or ERα as indicated by arrows. Note specific immunoprecipitation of DBC-1 by ERα-specific antibodies and ERα by DBC-1-specific antibodies only in the absence, but not in the presence, of estrogen. Results are representative of at least three independent experiments. For FIG. 1D, T-47D (top panel) and BG-1 (bottom panel) cells cultured in hormone-free medium for three days were treated without (−E2) or with (+E2) 17-β-estradiol ($10^{-7}$ M) for one hour prior to cell harvest and immunoprecipitation of whole cell lysates with antibodies specific for ERα Immunoprecipitates were resolved by SDS-10%-PAGE and processed by immunoblot analysis using antibodies specific for DBC-1 or ERα as indicated by arrows. Results are representative of at least three independent experiments.

In FIG. 8A, nuclear extracts (NEXT) from hormone-deprived fERα/S3 cells treated without (−E2) or with (+E2) 17-β-estradiol ($10^{-7}$ M) for twenty-four hours were chromatographed in parallel on phosphocellulose (PC-11) columns using a step gradient elution of increasing salt (KCl) concentration. Individual step fractions (40 pg) were resolved by SDS-10%-PAGE and processed by immunoblot analysis using an ERα-specific antibody (HC-20). FIG. 8B shows a fractionation and immunopurification scheme from hormone-deprived fERαlS3 and parental HeLaS3 cell nuclear extracts. In FIG. 8C, 0.3 M KCl step fractions derived from PC-11 chromatography of hormone-deprived fERα/S3 and HeLaS3 cell nuclear extracts (input) were subjected, in parallel, to anti-FLAG M2 monoclonal antibody affinity chromatography and elution with FLAG peptide (FLAG eluate). Peptide eluates were resolved by SDS-10%-PAGE and processed by silver staining. Additionally, size-selected ERAP pools were subjected to mass spectrometric based-peptide sequence analysis. Arrows identify ERα and DBC-1.

In FIG. 10A, harvested cells were stained with Annexin V-FITC and propidium iodide prior to quantification of apoptosis by flow cytometric analysis. Error bars represent the SD from the average of at least three independent experiments performed in triplicate. In FIG. 10B, cell lysates from representative apoptosis assays were resolved by SDS-10%-PAGE and processed by immunoblot analysis with antibodies specific for DBC-1, ERα or TFIIEβ (loading control) to validate DBC-1 knockdown.

DETAILED DESCRIPTION

Figure 1A:
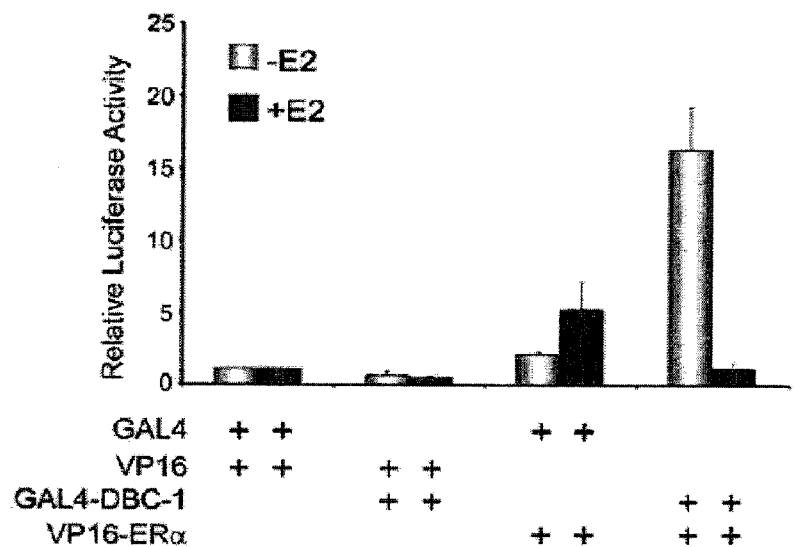
FIGS. 1A-D show DBC-1 and ERα interact in vivo in a ligand-independent manner.

Certain cancers, such as prostate, ovarian, endometrial and breast cancer, can be treated by hormone therapy (also called endocrine therapy), i.e. with hormones or anti-hormone drugs that slow or stop the growth of certain cancers by blocking the body's natural hormones. Hormone therapy is used synonymously herein with endocrine therapy. Such cancers may develop resistance, or be intrinsically resistant, to hormone therapy. The present application provides methods for the diagnosis and treatment of hormone-resistant or hormone-refractory cancers. As used herein the term resistance includes inherent resistance (de novo resistance) and resistance acquired during treatment (acquired resistance) either to hormones or to anti-hormone drugs.

In breast cancer, the emergence of endocrine resistance is coincident with a shift from ligand-dependent to ligand-independent control of ERα-regulated breast cancer cell growth and survival. As described herein, the deleted in breast cancer-1 gene product, DBC-1 (KIAA1967) was identified to be a direct ligand-independent binding partner of ERα.

The gene encoding DBC-1 was originally identified during a genetic search for candidate breast tumor suppressor genes on a human chromosome 8p21 region frequently deleted in breast cancers. Refined deletion analysis within this region revealed a second gene, deleted in breast cancer 2 (DBC-2), to encode a likely breast tumor suppressor, and confirmed that DBC-1 expression is not substantially extinguished in cancers from any source (Hamaguchi et al., PNAS 99:13647-52 (2002)). A search of the Oncomine database of published cancer microarray data (www.Oncomine.org), which currently permits analysis of gene expression data derived from 132 DNA microarray datasets among 24 different cancer types, reveals DBC-1 to be statistically significantly upregulated in breast carcinoma versus normal breast tissue as well as breast ductal carcinoma versus other cancers (Radvanyi et al., PNAS 102:11005-10 (2005); Biiner, Nat. Biotechnol. 23:183-4 (2005)). DBC-1 was also found in three independent studies totaling 369 breast tumor samples to be statistically significantly overexpressed in ER-positive versus ER-negative breast tumors (van de Vijver et al., N. Engl. J. Med. 347:1999-2009 (2002); Zhao et al., Mol. Biol. Cell 15:2523-36 (2004); Richardson et al., Cancer Cell 9:121-32 (2006)).

DBC-1 has been linked physically to the TNF-α/NFκB pathway by proteomic analysis (Bouwmeester et al., Nat. Cell Biol. 6:97-105 (2004)), while caspase-dependent processing of DBC-1 early in apoptosis induced by diverse stimuli, including TNF-α, was shown to unmask a proapoptotic function for the DBC-1 carboxyl terminus in the cytosol of moribund cells (Sundararajan et al., Oncogene 11:11 (2005)). Full-length DBC-1 is predominantly localized to the nucleus of healthy cells, and its normal biological function therein has heretofore remained unknown.

The present application describes that DBC-1 is a ligand independent ERα-interacting protein and that DBC-1 depletion reduced the steady-state level of unliganded ERα protein. DBC-1 amino terminus binds directly to the ERα hormone-binding domain both in vitro and in vivo in a strict E2-independent manner. Furthermore, DBC-1 depletion triggered apoptosis in cancer cells in the absence of hormone. E2-mediated disruption of the interaction between DBC-1 and unliganded ERα abrogated the increase in MCF-7 cell apoptosis observed to accompany DBC-1 knockdown, showing that DBC-1-bound ERα functions to suppress hormone-independent apoptosis. Therefore, ERα bound by DBC-1 promotes breast cancer cell growth and survival in the absence of hormone. These findings, described in detail in the Examples below, establish that DBC-1 modulates ERα expression and survival activity and identifies DBC-1 as a endocrine response determinant and therapeutic target in breast cancer.

Provided herein is a method of determining whether a cancer cell is sensitive to endocrine therapy comprising obtaining a population of cancer cells and determining the level of expression or activity of DBC-1 in the cells. An increase in expression or activity of DBC-1 as compared to a control indicates that the cancer cells are not sensitive to endocrine therapy. A decrease in expression or activity of DBC-1 as compared to control indicates that the cancer cells are sensitive to endocrine therapy.

Also provided is a method of determining whether a cancer cell is sensitive to endocrine therapy comprising obtaining a population of cancer cells and determining the presence of binding of DBC-1 and ERα. The presence of binding of DBC-1 and ERα as compared to a control indicates that the cancer cells are not sensitive to endocrine therapy. The absence of binding of DBC-1 and ERα indicates that the cancer cells are sensitive to endocrine therapy.

Provided herein is a method of determining whether a subject with cancer is suitable for treatment with endocrine therapy comprising obtaining a biological sample comprising cancer cells from the subject and determining the level of expression or activity of DBC-1. An increase in expression or activity of DBC-1 as compared to a control indicates that the subject is not suitable for treatment with endocrine therapy. A decrease in expression or activity of DBC-1 as compared to a control indicates that the subject is suitable for treatment with endocrine therapy.

Also provided herein is a method of determining whether a subject with cancer is suitable for treatment with endocrine therapy comprising obtaining a biological sample comprising cancer cells from the subject and determining the presence of binding of DBC-1 and ERα. The presence of binding of DBC-1 and ERα as compared to a control indicates that the subject is not suitable for treatment with endocrine therapy. The absence of binding of DBC-1 and ERα as compared to a control indicates that the subject is suitable for treatment with endocrine therapy.

Provided herein is a method of determining a susceptibility to hormone resistant cancer in a subject comprising obtaining a biological sample comprising cancer cells from the subject and determining the level of expression or activity of DBC-1. An increase in expression or activity of DBC-1 as compared to a control indicates that the subject is susceptible to hormone resistant cancer. A decrease in expression or activity of DBC-1 as compared to a control indicates that the subject is not susceptible to hormone resistant cancer.

Also provided is a method of determining a susceptibility to hormone resistant cancer in a subject comprising obtaining a biological sample comprising cancer cells from the subject and determining the presence of binding of DBC-1 and ERα. The presence of binding of DBC-1 and ERα as compared to a control indicates that the subject is susceptible to hormone resistant cancer. The absence of binding of DBC-1 and ERα as compared to a control indicates that the subject is not susceptible to hormone resistant cancer.

A method of inducing apoptosis of cancer cells is provided comprising selecting a population of hormone resistant cancer cells and contacting the hormone resistant cancer cells with an agent that inhibits expression of DBC-1. Also provided is a method of inducing apoptosis of cancer cells comprising selecting a population of hormone resistant cancer cells and contacting the hormone resistant cancer cells with an agent that inhibits binding of DBC-1 and ERα.

A method of treating hormone resistant cancer in a subject is provided comprising selecting a subject with hormone resistant cancer and administering an agent that inhibits expression of DBC-1 to the subject. Also provided is a method of treating hormone resistant cancer in a subject comprising selecting a subject with hormone resistant cancer and administering an agent that inhibits binding of DBC-1 and ERα to the subject.

A method of reducing susceptibility of acquiring hormone resistant cancer in a subject is provided comprising selecting a subject with hormone sensitive cancer and administering an agent that inhibits expression of DBC-1 to the subject.

Preferably, the agents used in the provided methods are administered in an effective amount to induce apoptosis of the hormone resistant cancer cells. The agent is also preferably comprised within a composition comprising the agent and a pharmaceutically acceptable carrier. The inhibitors of DBC-1 expression or DBC-1/ERα binding used in the provided methods can be, but are not limited to, a variety of functional nucleic acids, antibodies, proteins, and small molecules. The inhibitor can be, for example, an inhibitory peptide or an inhibitory nucleic acid. The inhibitory nucleic acid can be, but is not limited to, an siRNA. The inhibitory peptide optionally binds to the ERα binding domain of DBC-1. Inhibitors of DBC-1 expression or DBC-1/ERα binding can be further combined with other therapies, such as chemotherapy and/or radiotherapy. The subject of the provided methods can have endometrial cancer, breast cancer, ovarian cancer, prostate cancer, hormone sensitive cancer or hormone independent cancer.

The cancer cells used in the provided methods express one or more hormone receptors such as, for example, progesterone receptor, androgen receptor and estrogen receptor. The term presence of binding refers to the detection of binding of DBC-1 and ERα in hormone resistant cancer cells as compared to the absence of binding in hormone sensitive cancer cells or normal cells. The increase in expression of DBC-1 can be detected by measuring DBC-1 mRNA or protein using methods well known to those of skill in the art such as, for example, Northern and Western blots. DBC-1 can also be detected by immunochemical methods such as, for example, immunoblots and immunohistochemical staining, using an antibody that binds DBC-1 or ERα. Provided herein is an antibody (monoclonal or polyclonal) that binds DBC-1 in the region of amino acids 475-923.

The terms higher, increases, elevates, or elevation refer to increases above a control. For example, a control level can be the level of expression or activity in the same cell prior to or after recovery from a stimulus, or the control level can be the level in a control cell or population of cells in the absence of a stimulus.

As used herein the term cancer cells includes all cancer cells such as, for example, hormone resistant cancer cells, hormone sensitive cancer cells, endometrial cancer cells, breast cancer cells, ovarian cancer cells and prostate cancer cells. The breast, prostate, endometrial or ovarian cancer cells can be hormone sensitive or hormone resistant.

As used herein the term hormone resistant cancer cells includes cancer cells that are inherently resistant (de novo resistance) and cancer cells that have acquired resistance during treatment (acquired resistance). Preferably, the hormone resistant cancer cells express one or more hormone receptors. As used herein the term hormone receptors refers to a protein on the surface of a cell that binds to a specific hormone. Such receptors include, but are not limited to, progesterone receptor (PR), androgen receptor (AR) and estrogen receptor (ER).

Proteins, peptides or polypeptides can be used to inhibit DBC-1 expression or DBC-1/ERα binding. The term peptide, polypeptide, protein or peptide portion is used broadly herein to mean two or more amino acids linked by a peptide bond.

The term fragment is used herein to refer to a portion of a full-length polypeptide or protein. It should be recognized that the term polypeptide is not used herein to suggest a particular size or number of amino acids comprising the molecule and that a peptide of the invention can contain up to several amino acid residues or more. Preferably, the peptide that inhibits DBC-1/ERα binding binds to the ERα binding domain of DBC-1. As used herein the term ERα binding domain includes amino acids 1 to 150 of DBC-1. Thus, the peptide can bind DBC-1 in the region of amino acids 1 to 150 of DBC-1.

Peptides that can be used to inhibit DBC-1/ERα binding include amino acids 1-595 of ERα or amino acids 302-595 of ERα or fragments and variants thereof. Thus, the peptide can begin with any amino acid from 1 to 590 and end with amino acid 595. The peptide can also begin with any amino acid from 302 to 590 and end with amino acid 595 of ERα. The amino acid and nucleic acid sequences of ERα can be found at GenBank Accession Nos. NP_000116.2 and NM_000125.2, respectively. Fragments, variants, or isoforms of the ERα peptides are provided including functional variants as long as the fragments, variants, functional variants and isoforms inhibit DBC-1/ERα binding. Peptides can be tested for their ability to inhibit DBC-1/ERα binding by methods known to those of skill in the art, such as, for example, immunoassays, and the assay methods provided herein.

It is understood that the nucleic acids that can encode the aforementioned peptide sequences, variants and fragments thereof are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. Those skilled in the art will understand that a wide variety of expression systems may be used to produce ERα peptides as well as fragments, isoforms, and variants. Such peptides are selected based on their ability to inhibit DBC-1/ERα binding.

Proteins that inhibit DBC-1 expression or DBC-1/ERα binding also include antibodies with antagonistic or inhibitory properties. Such antibodies are selected from antibodies that bind the receptor itself or antibodies that bind a ligand of the receptor. In addition to intact immunoglobulin molecules, fragments, chimeras, or polymers of immunoglobulin molecules are also useful in the methods taught herein, as long as they are chosen for their ability to bind DBC-1, inhibit DBC-1 expression or DBC-1/ERα binding. The antibodies can be tested for their desired activity using in vitro assays, or by analogous methods, after which their in vivo therapeutic or prophylactic activities are tested according to known clinical testing methods. Antibodies to DBC-1 can also be used in the provided diagnostic methods for determining the level or activity of DBC-1 protein.

The term antibody is used herein in a broad sense and includes both polyclonal and monoclonal antibodies. Monoclonal antibodies can be made using any procedure that produces monoclonal antibodies. For example, disclosed monoclonal antibodies can be prepared using hybridoma methods, such as those described by Kohler and Milstein, Nature, 256: 495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,551 to Barbas et al.

Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The antibody fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term antibody or antibodies can also refer to a human antibody and/or a humanized antibody. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86 95, 1991). Human antibodies (and fragments thereof) can also be produced using phage display libraries (Hoogenboom et al., J. Mol. Biol., 227:381, 1991; Marks et al., J. Mol. Biol., 222: 581, 1991). The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551 255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non human antibody (or a fragment thereof) is a chimeric antibody or antibody chain that contains a portion of an antigen binding site from a non-human (donor) antibody integrated into the framework of a human (recipient) antibody. Fragments of humanized antibodies are also useful in the methods taught herein. As used throughout, antibody fragments include Fv, Fab, Fab', or other antigen binding portion of an antibody. Methods for humanizing non human antibodies are well known in the art. For example, humanized antibodies can be generated according to the methods of Winter and co workers (Jones et al., Nature, 321:522 525 (1986), Riechmann et al., Nature, 332:323 327 (1988), Verhoeyen et al., Science, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Also provided herein are functional nucleic acids that inhibit expression of DBC-1. Such functional nucleic acids include but are not limited to antisense molecules, aptamers, ribozymes, triplex forming molecules, RNA interference (RNAi), and external guide sequences. Thus, for example, a small interfering RNA (siRNA) could be used to reduce or eliminate expression of DBC-1.

Functional nucleic acids are nucleic acid molecules that have a specific function, such as binding a target molecule or catalyzing a specific reaction. Functional nucleic acid molecules can interact with any macromolecule, such as DNA, RNA, polypeptides, or carbohydrate chains. Thus, functional nucleic acids can interact with the mRNA, genomic DNA, or polypeptide. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Representative examples of how to make and use aptamers to bind a variety of different target molecules can be found in, for example, U.S. Pat. Nos. 5,476,766 and 6,051,698.

Ribozymes are nucleic acid molecules that are capable of catalyzing a chemical reaction, either intramolecularly or intermolecularly. There are a number of different types of ribozymes that catalyze nuclease or nucleic acid polymerase type reactions which are based on ribozymes found in natural systems, such as hammerhead ribozymes, hairpin ribozymes and tetrahymena ribozymes). There are also a number of ribozymes that are not found in natural systems, but which have been engineered to catalyze specific reactions de novo (for example, but not limited to U.S. Pat. Nos. 5,807,718, and 5,910,408). Ribozymes may cleave RNA or DNA substrates. Representative examples of how to make and use ribozymes to catalyze a variety of different reactions can be found in U.S. Pat. Nos. 5,837,855, 5,877,022, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. Representative examples of how to make and use triplex forming molecules to bind a variety of different target molecules can be found in U.S. Pat. Nos. 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit (Ambion, Austin, Tex.).

Methods of screening for agents that inhibit expression of DBC-1 are provided. Such a screening method comprises the steps of providing a cell that expresses DBC-1; contacting the cell with a candidate agent to be tested; and quantifying the expression of DBC-1. The contacting step can be in vitro.

Methods of screening for agents that inhibit DBC-1/ERα binding are also provided. Such a screening method comprises the steps of providing a cell that expresses ERα and DBC-1, wherein DBC-1 and ERα bind within the cell; contacting the cell with a candidate agent to be tested; and determining whether the candidate agent disrupts or prevents binding of DBC-1 and ERα. Another method of screening for agents that inhibit DBC-1/ERα binding comprises the steps of providing a sample comprising ERα and DBC-1, wherein DBC-1 is capable of binding ERα in the sample; contacting the sample with a candidate agent to be tested; and determining whether the candidate agent disrupts binding of DBC-1 and ERα.

Such methods allow one skilled in the art to select candidate agents that exert a regulating effect on the expression level of DBC-1 or the binding of DBC-1 and ERα. Such agents may be useful as active ingredients included in pharmaceutical compositions for treating patients suffering from cancer. The cell in the methods above can be a cell that normally expresses DBC-1 and/or ERα. The cell can be a hormone resistant cancer cell that expresses DBC-1 and ERα. The cell can also be a prokaryotic or an eukaryotic cell that has been transfected with a nucleotide sequence encoding DBC-1 and/or ERα or a variant or a fragment thereof, operably linked to a promoter. Using DNA recombination techniques well known by the one skill in the art, protein encoding DNA sequences can be inserted into an expression vector, downstream from a promoter sequence.

Quantification of expression of DBC-1 may be realized either at the mRNA level or at the protein level. In the latter case, antibodies may be used to quantify the amounts of DBC-1 protein, for example in an ELISA or a RIA assay. Quantification of DBC-1 mRNA may be realized by a quantitative PCR amplification of the cDNA obtained by a reverse transcription of the total mRNA of the cell expressing DBC-1, using a pair of primers specific for DBC-1.

Methods for determining whether the candidate agent disrupts binding of DBC-1 and ERα are well known to those of skill in the art. The assay can be, for example, an immunoassay, radioimmunoassay (RIA), enzyme-linked immunosorbent assay (ELISA) and a non-competitive binding assay. Competitive binding assays wherein an unlabeled and a labeled analyte compete for sites to bind to a specific protein can also be used.

Pharmaceutical compositions comprising one or more of the inhibitors or agents provided herein may include carriers, thickeners, diluents, buffers, preservatives, surface active agents and the like in addition to the molecule of choice. Pharmaceutical compositions may also include one or more active ingredients such as antimicrobial agent, a chemotherapeutic agent, and the like. The compositions of the present application can be administered in vivo in a pharmaceutically acceptable carrier. By pharmaceutically acceptable is meant a material that is not biologically or otherwise undesirable. Thus, the material may be administered to a subject, without causing undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The disclosed compositions can be administered in a number of ways depending on whether local or systemic treatment is desired, and on the area to be treated. Thus, the disclosed compositions can be administered, for example, orally, parenterally (e.g., intravenously), by intramuscular injection, by intraperitoneal injection, transdermally, extracorporeally, or topically.

The materials may be in solution, suspension (for example, incorporated into microparticles, liposomes, or cells). These may be targeted to a particular cell type via antibodies, receptors, or receptor ligands. Suitable carriers and their formulations are described in Remington: The Science and Practice of Pharmacy (21th ed.) ed. David B. Troy, Lippincott Williams & Wilkins, 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8.5, and more preferably from about 7.8 to about 8.2. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of composition being administered.

The terms effective amount and effective dosage are used interchangeably. The term effective amount is defined as any amount necessary to produce a desired physiologic response. Effective amounts and schedules for administering the compositions may be determined empirically, and making such determinations is within the skill in the art. The dosage ranges for the administration of the compositions are those large enough to produce the desired effect in which the symptoms or disorder are affected. The dosage should not be so large as to cause substantial adverse side effects, such as unwanted cross-reactions, anaphylactic reactions, and the like. Generally, the dosage will vary with the age, condition, sex, type of disease and extent of the disease in the patient, route of administration, or whether other drugs are included in the regimen, and can be determined by one of skill in the art. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

The inhibitor of DBC-1 expression or DBC-1/ERα binding can be administered in combination with one or more other therapeutic or prophylactic regimens, such as, for example, chemotherapy. As used throughout, a therapeutic agent is a compound or composition effective in ameliorating a pathological condition. Illustrative examples of therapeutic agents include, but are not limited to, an anti-cancer compound, anti-inflammatory agents, anti-viral agents, anti-retroviral agents, anti-opportunistic agents, antibiotics, immunosuppressive agents, immunoglobulins, and antimalarial agents.

An anti-cancer compound or chemotherapeutic agent is a compound or composition effective in inhibiting or arresting the growth of an abnormally growing cell. Thus, such an agent may be used therapeutically to treat cancer as well as other diseases marked by abnormal cell growth. A pharmaceutically effective amount of an anti-cancer compound is an amount administered to an individual sufficient to cause inhibition or arrest of the growth of an abnormally growing cell. Illustrative examples of anti-cancer compounds include: bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, melphalan, methotrexate, mitomycin, 6-mercaptopurine, teniposide, 6-thioguanine, vincristine and vinblastine.

Inhibitors of DBC-1 expression or DBC-1/ERα binding can be further combined with other therapies, such as chemotherapy and/or radiotherapy in the treatment of malignancy, and therapeutic efficacy can be enhanced by apoptosis-inducing compounds.

Any of the aforementioned treatments can be used in any combination with the inhibitors described herein. Thus, for example, the inhibitors can be administered in combination with a chemotherapeutic agent and radiation. Other combinations can be administered as desired by those of skill in the art. Combinations may be administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents.

There are a variety of sequences related to, for example, DBC-1 and ERα that are disclosed on Genbank, at www.pubmed.gov and these sequences and others are herein incorporated by reference in their entireties as well as for individual subsequences contained therein. For example, the amino acid and nucleic acid sequences of DBC-1 (KIAA1967) can be found at GenBank Accession Nos. NP_066997.3 and NM_021174.4, respectively. The amino acid and nucleic acid sequences of ERα can be found at GenBank Accession Nos. NP_000116.2 and NM_000125.2, respectively.

The term isolated requires that the material be removed from its original environment (e.g., the natural environment if it is naturally occurring).

As used throughout, by a subject is meant an individual. Thus, the subject can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

Ranges may be expressed herein as from about one particular value, and/or to about another particular value. Similarly, when values are expressed as approximations, by use of the term about, it will be understood that the particular value is included. It will be further understood that the endpoints of each of the ranges are significant both in relation to the other endpoint, and independently of the other endpoint.

The absence of binding as used herein refers to a level of binding that is at or below detectable levels using detection methods known in the art and described herein. The absence of binding includes a level of binding that is about less that 1.5 times above background using detection methods. The presence of binding refers to a level of binding that is detectable and includes, for example, a level of binding that is about 1.5 times or greater above background levels using detection methods.

Inhibit, inhibiting, and inhibition mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein the terms treatment, treat or treating refers to a method of reducing the effects of a disease or condition or at least one symptom of the disease or condition. Thus in the disclosed method treatment can refer to a 10%, 20%, 30%, 40%, 50%, 60%, 70%, 80%, 90% or 100% reduction in the severity of an established disease or condition or symptom of the disease or condition. For example, the method for treating cancer is considered to be a treatment if there is a 10% reduction in one or more symptoms of the disease in a subject as compared to control. Thus the reduction can be a 10, 20, 30, 40, 50, 60, 70, 80, 90, 100% or any percent reduction in between 10 and 100 as compared to native or control levels. It is understood that treatment does not necessarily refer to a cure or complete ablation of the disease, condition or symptoms of the disease or condition.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of molecules of the inhibitor are discussed, each and every combination and permutation of inhibitor and the modifications that are possible are specifically contemplated unless specifically indicated to the contrary. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Publications cited herein and the material for which they are cited are hereby specifically incorporated by reference. No admission is made that any reference constitutes prior art. The discussion of references states what their authors assert, and applicants reserve the right to challenge the accuracy and pertinency of the cited documents.

EXAMPLES

Example 1

Disruption of DBC-1/ER-α Binding Promotes Apoptosis of Cancer Cells

Materials and Methods

Expression Plasmids. pCS2+-ERα was constructed by subcloning a BamHI-BamHI fragment carrying the full-length coding region of ERα cDNA from pG/ER(G) (Liu and Picard, FEMS Microbiol. Lett. 159:167-71 (1998)) into pCS2+ (Turner and Weintraub, Genes Dev. 8:1434-47 (1994)). pACT-ERα was constructed by subcloning a BamHI-BamHI fragment carrying the full-length coding region of ERα cDNA from pCS2+-ERα into the pACT VP16 fusion vector (Promega Corporation, Madison, Wis.). GST-ERα (1-184), GST-ERα (185-250), GST-ERα (251-301), and GST-ERα (302-595) were described previously (Qi et al., J. Biol. Chem. 277:28624-30 (2002)). GST-ERα (1-595) was generated by amplifying ERα by PCR and inserting it into the EcoRI site of pGEX-4T-3 vector (Amersham Biosciences, Piscataway, N.J.).

pSport1-DBC-1 was a clone obtained from RZPD German Resource Center for Genome Research GmbH (Berlin, Germany) (RZPD clone ID: DKFZp761O0817Q; KIAA1967).

pCS2+DBC-1 was constructed by first amplifying the amino terminal half of DBC-1 by PCR and inserting it into the ClaI/EcoRI site of pCS2+.His6.FLAG, which yielded pCS2+ .His6.FLAG-5'DBC-1.SphI. The carboxyl terminal half of DBC-1 was amplified by PCR and then inserted into the SphI/EcoRI site of pCS2+.His6.FLAG-5'DBC-1.SphI to yield pCS2+DBC-1, which contains a STOP codon between the DBC-1 coding sequence and the His6.FLAG fusion. This construct was confirmed by sequencing. pCS2+.His6.FLAG-DBC-1 was generated by amplifying the carboxyl terminal half of DBC-1 by PCR and then inserting it into the SphI/EcoRI site of pCS2+.His6.FLAG-5'DBC-1.SphI to create a version of DBC-1 fused to C-terminal 6xHis and FLAG tags. pCS2+-DBC-1 amino-terminal fragments (1-478, 1-300, 1-230, 1-200, 1-150, and 150-478) were generated by amplifying fragments by PCR and inserting them into the EcoRI/XhoI site of pCS2+. pCS2+-DBC-1 (479-923) was generated by amplifying the carboxyl terminal half of DBC-1 by PCR and inserting it into the EcoRI/XhoI site of pCS2+. pBIND-DBC1 (1-478) was constructed by amplifying the amino terminal half of DBC-1 by PCR and inserting it into the SalI/XbaI site of the pBIND GAL4 fusion vector (Promega Corporation, Madison, Wis.). pBINDDBC1 (479-923) was constructed by amplifying the carboxyl terminal half of DBC-1 by PCR and inserting it into the XbaI/NotI site of pBIND. pBIND-DBC-1 was constructed by subcloning an XbaI/NotI carboxyl terminal fragment of DBC-1 from pBIND-DBC1 (479-923) into pBIND-DBC1 (1-478).

Reporter Plasmids. pG5luc, carrying five GAL4 DNA-binding sites upstream of the major late promoter of adenovirus driving expression of the firefly luciferase gene, was purchased from Promega Corporation, Madison, Wis.

Cell Lines and Culture Conditions. The HeLa (ATCC, Manassas, Va.), T-47D (ATCC, Manassas, Va.), MCF-7 (ATCC, Manassas, Va.), AmphoPack 293 (Clontech, Mountain View, Calif.), and MDA-MB-231 (ATCC, Manassas, Va.) cells were routinely cultured in Dulbecco's modified Eagle medium (Gibco BRL, Gaithersburg, Md.) supplemented with 10% fetal bovine serum (Hyclone, Logan, Utah) and penicillin-streptomycin-L-glutamine (Gibco BRL, Gaithersburg, Md.). BG-1 cells, (Ignar-Trowbridge et al., Mol. Endocrinol. 7:992-8 (1993)), were routinely cultured in Dulbecco's modified Eagle medium:F12 (Gibco BRL, Gaithersburg, Md.) supplemented as listed above. All cell lines except BG-1 and MDA-MB-231 cells were cultured at 37° C. in a 10% CO2 humidified chamber; BG-1 and MDA-MB-231 cells were cultured at 5% CO2.

GST Pull-down Assays. GST and GST fusion proteins were expressed in and purified from BL21-CodonPlus(DE3)-RIPL *Escherichia coli* (Stratagene, La Jolla, Calif.). Cells were grown at 37° C. to A600 of 1.0, then isopropyl-1-thio-β-D-galactopyranoside (IPTG) was added to a final concentration of 0.5 mM. For GST, GST-ERα (1-184), GST-ERα (185-250), and GST-ERα (251-301), the cells were grown at 30° C. for another 5 hours. For GST-ERα (302-595), the cells were grown at 20° C. for another 5 hours. For GST-ERα (1-595), the cells were grown at 16° C. for another 5 hours. Cells were pelleted, washed once with phosphate buffered saline, and resuspended in lysis 250 buffer (50 mM Tris-HCl, 250 mM NaCl, 5 mM EDTA, 0.1% NP-40) supplemented with protease inhibitors (20 μM antipain, 2 μM pepstatin, 20 μM leupeptin, 2 μg/ml aprotinin). Resuspended cells were subjected to one round of freeze-thaw followed by sonication and clarification by centrifugation at 35,000×g for 30 min at 4° C. Clarified GST lysates were bound to glutathione-Sepharose beads (Amersham Biosciences, Piscataway, N.J.) for 45 min at 25° C., followed by washing four times for 5 min each with lysis 250 buffer containing 0.2% bovine serum albumin (BSA) and protease inhibitors. DBC-1 or fragments of DBC-1 were labeled with [35S]methionine (TNT SP6 quick coupled transcription/translation system; Promega Corporation, Madison, Wis.) and incubated with immobilized GST proteins in PD buffer (50 mM Tris-HCl, 200 mM KCl, 5 mM MgCl$_2$, 5 mM EDTA, 0.05% NP-40) for 2 h at 4° C. Binding reactions were washed with PD buffer three times for 5 min each at 4° C. and subsequently boiled in 20 μl of 1× Laemmli sample buffer. Eluates were resolved by SDS-12%-PAGE and visualized by PhosphorImager analysis (Amersham Biosciences, Piscataway, N.J.).

Mammalian Two-Hybrid Interaction Analysis. HeLa cells grown under hormone-free conditions for two days were plated at 1×10$^5$ cells per well in 12-well plates (Corning, Corning, N.Y.). After 24 hours, the cells were transfected using FuGENE® 6 (Roche, Basel, Switzerland) according to the manufacturer's recommendations. In defining the ERα-DBC-1 interaction, transfection mixtures consisted of pCH110 (Zheng et al., PNAS 98:9587-92 (2001)), an internal control plasmid, expressing β-galactosidase under control of the SV40 promoter (167 ng), pG5luc reporter (167 ng), pACT-ERα (334 ng), and the various pBIND-DBC-1 constructs (334 ng), including pBIND-DBC-1, pBIND-DBC-1 (1-478), and pBIND-DBC-1 (479-923). pBIND empty vector was used as an appropriate control for interaction with pACT-ERα. pACT empty vector was used as an appropriate control for interaction with the various pBIND-DBC-1 constructs. After 48 hours, cells were harvested and assayed for luciferase activity according to the manufacturer's guidelines (Promega Corporation, Madison, Wis.). Luciferase activity was corrected for the corresponding β-galactosidase activity to give relative activity. β-galactosidase activity was assayed according to manufacturer's instructions (Tropix, Bedford, Mass.). Transfections were repeated a minimum of three times in duplicate. For experiments with ligand treatment, 17-β-estradiol (E2; Sigma-Aldrich, St. Louis, Mo.) was added to cells at 10$^{-7}$ M for 24 hours prior to harvest.

For Western blot analysis, 48 hours posttransfection, whole cell lysates were prepared in RIPA buffer (50 mM Tris-HCl, 150 mM NaCl, 0.5% deoxycholate, 1% NP-40, 0.1% SDS) supplemented with protease inhibitors and clarified by centrifugation. Equivalent amounts of lysates were boiled in Laemmli sample buffer and resolved by SDS-10%-PAGE. Proteins were analyzed by immunoblot using antibodies against GAL4-DBD (RK5C1; Santa Cruz, Santa Cruz, Calif.) and ERα (HC-20; Santa Cruz, Santa Cruz, Calif.).

Co-immunoprecipitations. T-47D, MCF-7, or BG-1 cells were grown under hormone-free conditions for three days and treated without or with 17-β-estradiol (10$^{-7}$ M) or 4-hydroxytamoxifen (10$^{-6}$ M; Sigma-Aldrich, St. Louis, Mo.) or ICI 182,780 (10$^{-7}$ M; Tocris, Ellisville, Mo.) for one hour prior to cell harvest and co-immunoprecipitation. Whole cell lysates were prepared in 0.5% NP-40 lysis buffer (50 mM Tris-HCl, 150 mM NaCl, 5 mM EDTA, 0.5% NP-40) supplemented with protease inhibitors and clarified by centrifugation. Nuclear and cytoplasmic extracts were prepared as described (Dignam et al., Nucleic Acid Res. 11:1475-89 (1983)). Lysates were adjusted to binding buffer (50 mM Tris-HCl, 175 mM NaCl, 5 mM EDTA, 0.2% NP-40, 10% glycerol, supplemented with protease inhibitors) concentration. Lysates were then subjected to immunoprecipitation with rabbit polyclonal anti-ERα (HC-20; Santa Cruz, Santa Cruz, Calif.) antibody or mouse polyclonal anti-DBC-1 antibody (produced in our laboratory against recombinant DBC-1 (amino acids 475-923)) and protein A Sepharose beads.

Immune complexes were washed three times with binding buffer, boiled in Laemmli sample buffer, and resolved by SDS-10%-PAGE. Proteins were transferred to nitrocellulose membranes and visualized by using antibodies against DBC-1, ERα, HSP90 (rabbit polyclonal; GeneTex, San Antonio, Tex.), CYP40 (rabbit polyclonal; AbCam, Cambridge, Mass.), appropriate peroxidase-conjugated secondary antibodies (Biorad, Hercules, Calif.), and enhanced chemiluminescence detection (Amersham Biosciences, Piscataway, N.J.).

DBC-1 Silencing by siRNA. To selectively knockdown the expression of endogenous DBC-1 protein, an siRNA pool consisting for 4 different target sequences was used (catalog #D-010427-01 sense sequence CAACUGGUGUGGC-UACUUGUU (SEQ ID NO:1), antisense sequence 5'-PCAAGUAGCCACACCAGUUGUU (SEQ ID NO:2); catalog #D-010427-02 sense sequence CUACUGAGCCU-UCCUGAAAUU (SEQ ID NO:3), antisense sequence 5'-PU-UUCAGGAAGGCUCAGUAGUU (SEQ ID NO:4); catalog #D-010427-03 sense sequence CAGCUUGCAUGAC-UACUUUUU (SEQ ID NO:5) antisense sequence 5'-PAAAGUAGUCAUGCAAGCUGUU (SEQ ID NO:6); catalog #D-010427-04 sense sequence CAGCGGGUCU-UCACUGGUAUU (SEQ ID NO:7) antisense sequence 5'-PUACCAGUGAAGACCCGCUGUU (SEQ ID NO:8); Dharmacon, Chicago, Ill.).

These RNA duplexes (3 µg per $2 \times 10^6$ cells), as well as a negative control duplex that does not pair with any human mRNA (Dharmacon, Chicago, Ill.), were electroporated in MCF-7 or MDA-MB-231 cells using the cell line Nucleofector® kit V (Amaxa, Gaithersburg, Md.). Immediately following control or DBC-1 siRNA electroporation, cells were seeded at a concentration of $1 \times 10^6$ per 60 mm plate. In all experiments, cells were allowed to grow for three days in phenol-red free medium supplemented with 10% charcoal/dextran-treated FBS and without or with indicated chemical treatments. Cells were harvested three days post-electroporation.

Western Blot Analysis. Three days postelectroporation, whole cell lysates were prepared in RIPA buffer (50 mM Tris-HCl, 150 mM NaCl, 0.5% deoxycholate, 1% NP-40, 0.1% SDS) supplemented with protease inhibitors and clarified by centrifugation. Lysates were boiled in Laemmli sample buffer and resolved by SDS-10%-PAGE. Proteins were analyzed by immunoblot using antibodies against DBC-1 (produced in our laboratory), ERα (HC-20; Santa Cruz, Santa Cruz, Calif.), and TFIIEβ (C-21; Santa Cruz, Santa Cruz, Calif.) as previously described. Quantification of Western blots was performed using the Kodak ImageStation 2000R.

Quantitative Real-Time RT-PCR. Three days post-electroporation, RNA was isolated from cells using TRIZOL® reagent (Invitrogen, Carlsbad, Calif.). RNA was reverse transcribed using random hexamers and SUPERSCRIPT® III (Invitrogen, Carlsbad, Calif.) following the manufacturer's instructions. Quantitative RT-PCR was performed using ABSOLUTE™ SYBR® Green ROX Mix (ABgene, Rochester, N.Y.) on an ABI PRISM 7900HT Fast real-time PCR system (Applied Biosystems, Foster City, Calif.). The gene-specific primers used were as follows: DBC-1 (5'-ATG TCC CAG TTT AAG CGC CAG-3' (SEQ ID NO:9) and 5'-CAA CCC CAA AGT AGT CAT GCA A-3' (SEQ ID NO:10)), ERα (5'-CCA CCA ACC AGT GCA CCA TT-3' (SEQ ID NO:11) and 5'-GGT CTT TTC GTA TCC CAC CTT TC-3' (SEQ ID NO:12)), and GAPDH (5'-CCT GTT CGA CAG TCA GCC G-3' (SEQ ID NO:13) and 5'-CGA CCA AAT CCG TTG ACT CC-3' (SEQ ID NO:14)).

Proliferation Assays. Three days prior to electroporation, cells were grown in phenol-red free medium supplemented with 10% charcoal/dextran-treated FBS. Immediately following control or DBC-1 siRNA electroporation, cells were seeded at a concentration of $10 \times 10^4$ per well in 6-well plates. In all experiments, triplicates of cells were allowed to grow for seven days in phenol-red free medium supplemented with 10% charcoal/dextran-treated FBS and without or with 17-β-estradiol ($10^{-7}$ M) at 37° C. and 10% $CO_2$. Cell viability was determined using the trypan blue exclusion assay, and viable cells were counted with the use of a hemacytometer. Proliferation assays were repeated a minimum of three times.

Apoptosis Assays. Three days prior to electroporation, cells were grown in phenol-red free medium supplemented with 10% charcoal/dextran-treated FBS. Immediately following control or DBC-1 siRNA electroporation, cells were seeded at a concentration of $1 \times 10^6$ per 60 mm plate. In all experiments, cells were allowed to grow for three days in phenol-red free medium supplemented with 10% charcoal/dextran-treated FBS and without or with 17-β-estradiol ($10^{-7}$ M), ICI 182,780 ($10^{-7}$ M; Tocris, Ellisville, Mo.), or a combination of the two at 37° C. and 10% $CO_2$. Seventy-two hours postelectroporation, trypsinized cells ($1 \times 10^5$) were stained with Annexin V-FITC (BD Pharmingen, San Jose, Calif.) and propidium iodide (Becton Dickison (BD), Franklin Lakes, N.J.) according to the manufacturer's instructions. Flowcytometric analyses to quantify apoptosis were done in a FACSCALIBUR™ (BD, Franklin Lakes, N.J.). All Annexin V-FITC positive cells were considered apoptotic. Apoptosis assays were repeated a minimum of three times.

Data Analysis. Statistical significance was assessed by comparing mean values (±SD) values with Student's t-test for independent groups. $p \leq 0.05$ was considered statistically significant.

Results

Figure 8A:
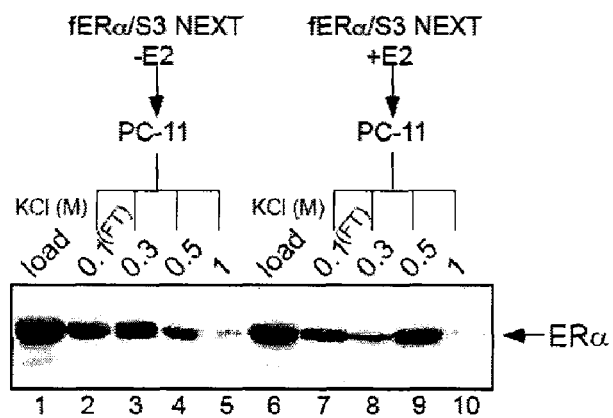
FIGS. 8A, 8B and 8C show biochemical purification of ligand-independent ERα-associated proteins (ERAPs).
Figure 8B:
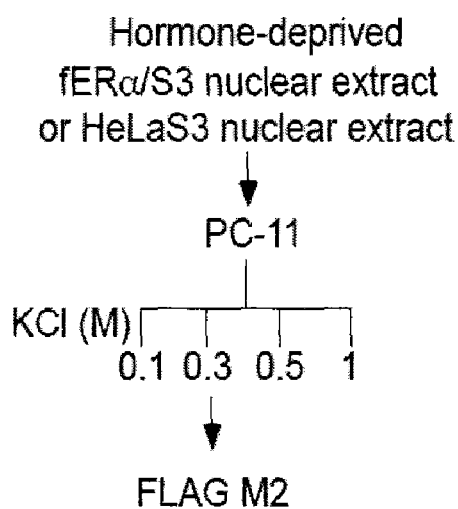
Figure 8C:
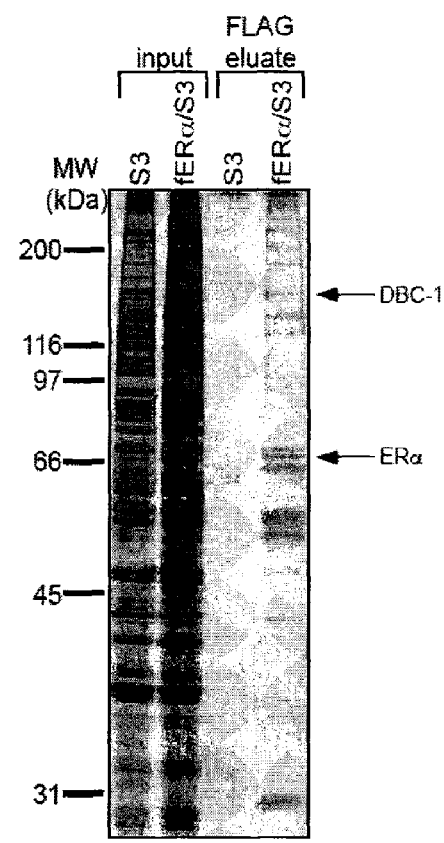

DBC-1 Interacts with ERα in vivo in a Ligand-Independent Manner. DBC-1 was identified by mass spectrometric-based peptide sequence analysis of proteins coimmunoprecipitated specifically with unliganded, but not liganded, ERα (FIGS. 8A, 8B and 8C). To facilitate the isolation of ERα-associated proteins, retroviral-mediated gene transfer to engineer a HeLaS3 human cervical carcinoma-derived cell line (fERalS3) that stably expresses a FLAG epitope-tagged ERα was employed (fERα). Initially, to characterize the chromatographic profile of fERα in these cells as a function of E2, nuclear extracts derived from hormone-deprived and hormone-stimulated fERα/S3 cells were fractionated by phosphocellulose (PC-11) chromatography. Individual step fractions were then analyzed by immunoblot analysis for the presence of fERα (FIG. 8A). This analysis revealed a marked ligand-induced shift in the chromatographic peak of fERα from a 0.3 M KCl step fraction in the absence of E2 to a 0.5 M KCl step fraction in the presence of E2 (FIG. 8A). This ligand-induced switch in the chromatographic profile of fERα is consistent with the exchange of fERα between ligand-independent and ligand-dependent protein partners.

To isolate ligand-independent ERα-associated proteins, the PC-11 0.3 M KCl step fraction from hormone deprived ERalS3 nuclear extracts was chromatographed on an anti-FLAG M2 monoclonal antibody affinity column. As a negative control, a comparable 0.3 M KCl step fraction from hormone-deprived parental HeLa S3 nuclear extracts was subjected to FLAG monoclonal antibody affinity chromatography (FIG. 8B). This procedure resulted in the specific isolation of fERα along with approximately 25 ERα-associated proteins (ERAPs) ranging in size from approximately 30 to 300 kDa (FIG. 8C). No ERAPs were recovered following M2 antibody affinity chromatography of partially purified nuclear extracts derived from the parental HeLaS3 cell line. This result indicates that ERAPs observed following M2 antibody affinity chromatography of partially purified fERα/S3 nuclear extracts were recovered by virtue of their specific association with FLAG epitope-tagged ERα. Mass spectrometric based peptide sequence analysis of size-selected ERAP pools revealed one ERAP to be the product of the Deleted in Breast Cancer-1 gene, DBC-1.

To determine if DBC-1 interacts directly with unliganded ERα in vitro, and to map the reciprocal binding domains on each protein, the ability of GST-ERA derivatives to bind to full-length DBC-1 or DBC-1 truncation fragments produced by in vitro translation was tested. DBC-1 bound most efficiently to GST-ERA derivatives 1-595 (full-length ERα) and 302-595 (Era hormone-binding domain). Reciprocally, GST-ERα 1-595 (full-length ERα) bound to the extreme amino-terminus of DBC-1 (amino acids 1-150).

Figure 1B:
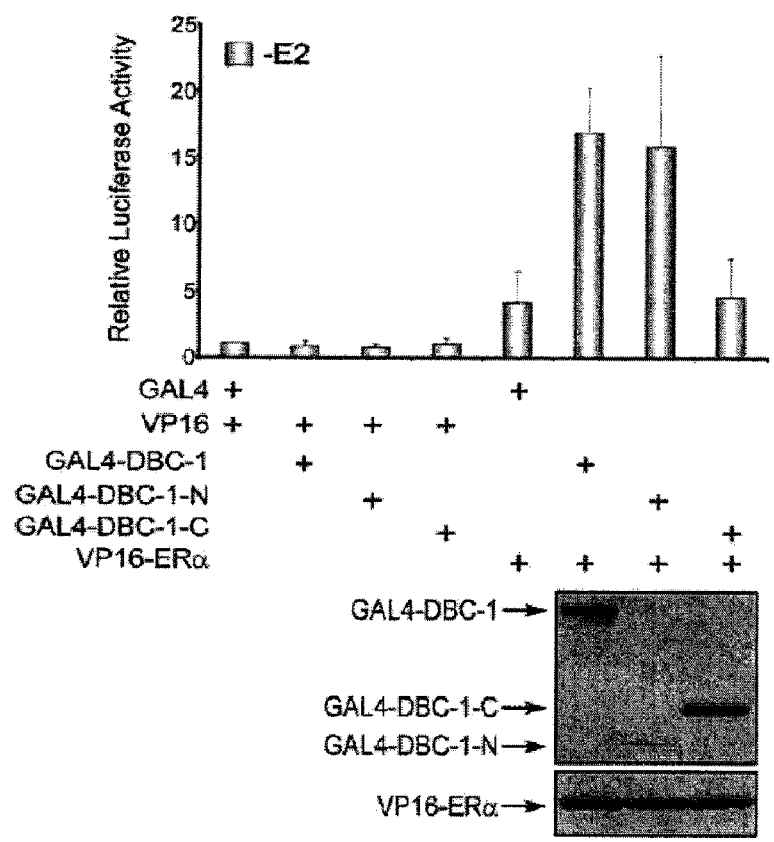

To validate the ligand-independent interaction between DBC-1 and ERα in vivo, a mammalian two-hybrid interaction analysis was employed. Chimeric proteins consisting of DBC-1 fused to the GAL4-DNA-binding domain and ERα fused to the VP16 activation domain were expressed with or without one another in HeLa cells and examined for their respective abilities to activate transcription from a reporter template controlled by GAL4 DNA-binding sites in both the absence and presence of E2. In the absence of E2, DBC-1 and ERα exhibited a robust interaction that was disrupted by addition of E2 to the cell culture medium (FIG. 1A). Further analysis of DBC-1 amino and carboxyl truncation derivatives revealed that the ligand-independent association between DBC-1 and ERα is mediated entirely by the amino terminal half of DBC-1 (amino acids 1-150) (FIG. 1B).

Figure 1C:
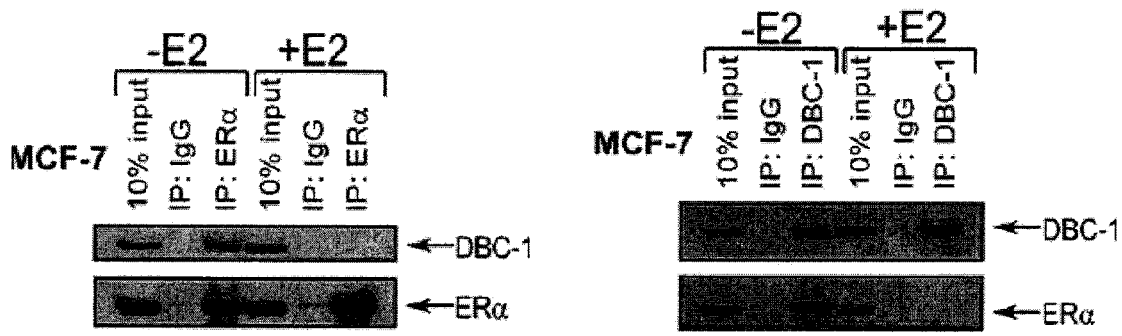
Figure 1D:
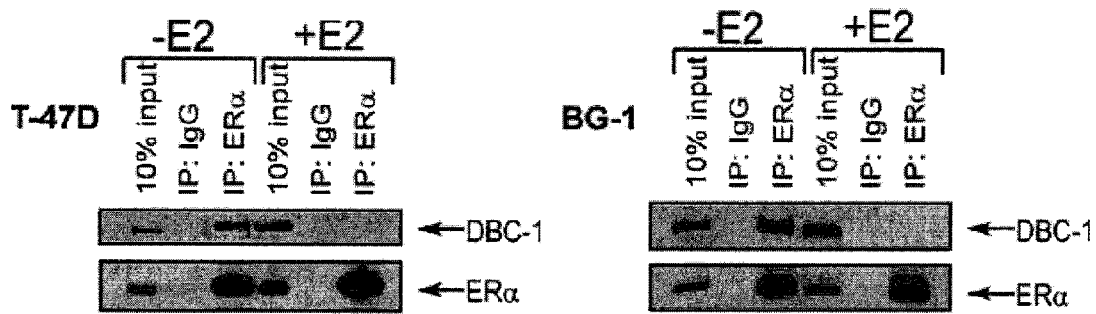

To confirm the ligand-independent in vivo association between DBC-1 and ERα, the ability of antibodies specific for ERα or DBC-1 to coprecipitate one another in MCF-7 human breast cancer cells, which express both ERα and DBC-1, was examined. This analysis revealed that DBC-1 was specifically and reciprocally co-immunoprecipitated along with unliganded, but not liganded, ERα, demonstrating that the two endogenous proteins interact in a strict ligand-independent manner in human breast cancer cells (FIG. 1C). The ligand independent interaction between endogenous DBC-1 and ERα was confirmed in both T-47D human breast and BG-1 human ovarian cancer cell lines, thus revealing the DBC-1/ERα interaction to be conserved in a variety of ERα-expressing cell lines (FIG. 1D).

Figures 2A, 2B:
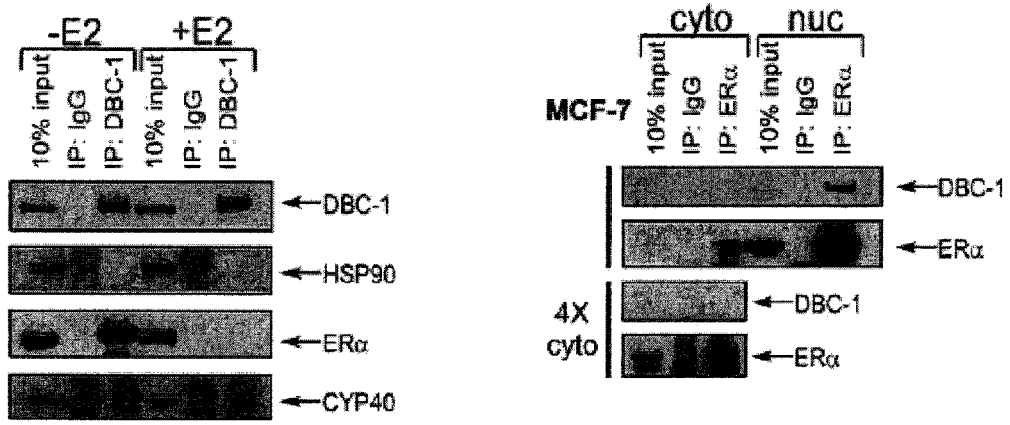
FIGS. 2A and 2B show via coimmunoprecipitation analysis that DBC-1 and unliganded ERα associate in the nucleus independently of HSP90. For FIG. 2A, MCF-7 cells cultured in hormone-free medium for three days were treated without (−E2) or with (+E2) 17-β-estradiol ($10^{-7}$ M) for one hour prior to cell harvest and immunoprecipitation of whole cell lysates with antibodies specific for DBC-1. Immunoprecipitates were resolved by SDS-10%-PAGE and processed for immunoblot analysis with antibodies specific for DBC-1, HSP90, ERα, or CYP40 as indicated by arrows. Results are representative of at least three independent experiments. For FIG. 2B, MCF-7 cells cultured in hormone-free medium for three days were fractionated into cytoplasmic (cyto) and nuclear (nuc) extracts. Equivalent amounts of each extract were immunoprecipitated with antibodies specific for ERα. Immunoprecipitates were resolved by SDS-10%-PAGE and processed for immunoblot analysis with antibodies specific for DBC-1 or ERα as indicated by arrows. Note that an additional immunoprecipitation containing four times the amount of cytoplasmic extract (4× cyto) failed to yield a detectable amount of DBC-1 in either the input or immunoprecipitate. Results are representative of at least three independent experiments.

HSP90 together with additional heat shock family members and immunophilins are known to form a heteromeric chaperone complex that sequesters neosynthesized and unliganded ERα in an inactive state, primes it for ligand-binding, and protects it from proteolytic degradation. The physical relationship between unliganded ERα in complex with HSP90-based chaperones and DBC-1 was examined by coimmunoprecipitation analysis using MCF-7 whole cell lysates. Whereas unliganded ERα immunoprecipitates included not only DBC-1, but also HSP90, DBC-1 immunoprecipitates included unliganded ERα, but neither HSP90 nor the immunophilin CYP40 (FIG. 2A). Thus, DBC-1 is not a component of the classical HSP90-based molecular chaperone complex. The subcellular pool of unliganded ERα in specific association with DBC-1 was identified by coimmunoprecipitation analysis using fractionated MCF-7 cell lysates. ERα/DBC-1 complexes were found exclusively in the nuclear fraction (FIG. 2B), thus revealing that unliganded ERα is distributed amongst at least two distinct protein complexes in human breast cancer cells, a cytosolic HSP90-based molecular chaperone complex and a nuclear DBC-1-containing protein complex.

Figure 3A:
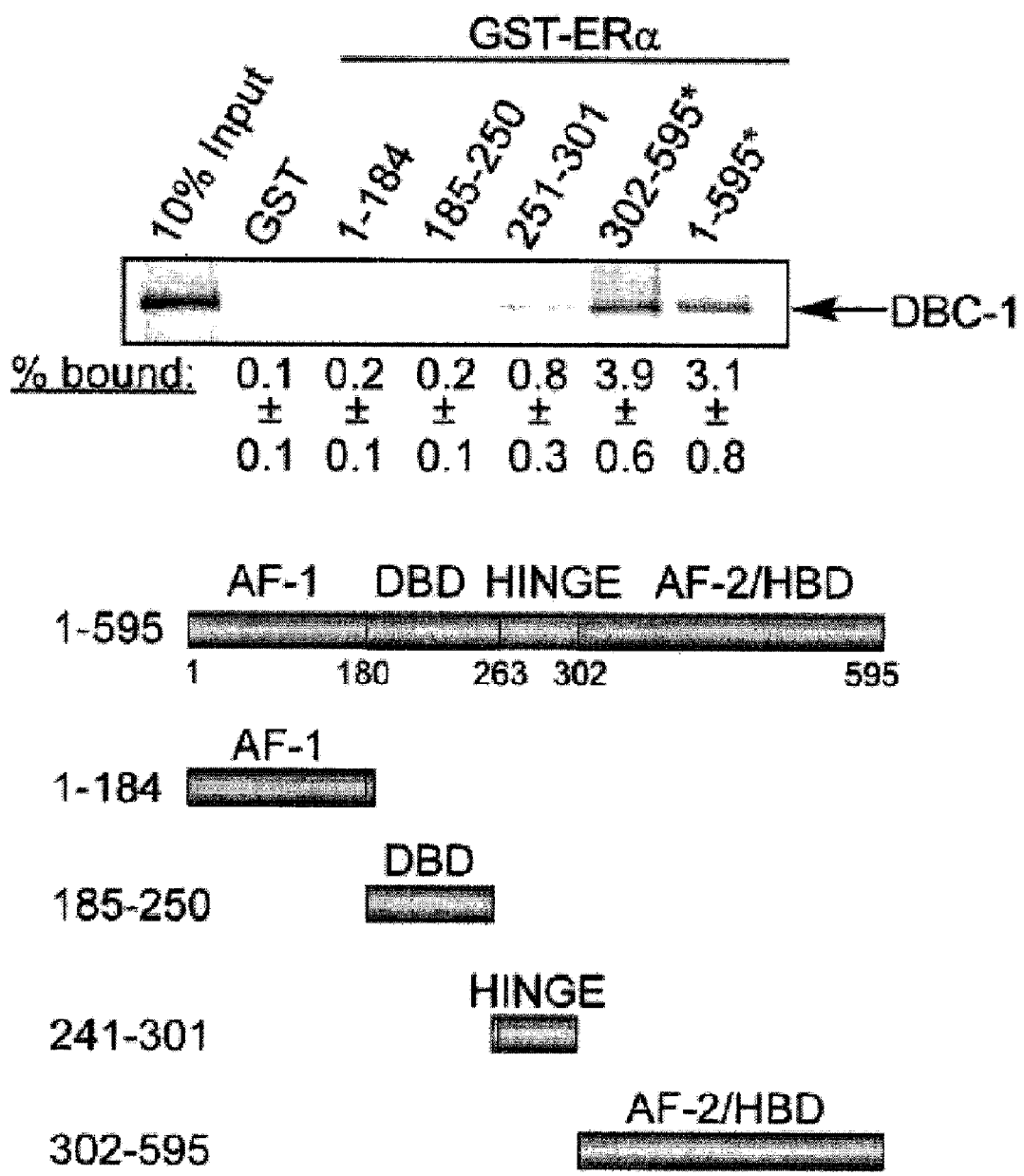
FIGS. 3A and 3B show via GST-pulldown assays that the DBC-1 N-terminus binds to the ERα hormone-binding domain in vitro. GST pulldown assays were performed using full-length in vitro translated DBC-1 and GST-ERα fragments (FIG. 3A) or in vitro translated DBC-1 fragments and GST-full-length ERα (FIG. 3B) as indicated. Numbers refer to amino acid coordinates. 35S-labeled in vitro translated proteins were incubated with glutathione-sepharose immobilized GST derivatives and bound proteins were resolved by SDS-12%-PAGE prior to detection by Phosphorimager analysis. Input represents 10% of the 35S-labeled in vitro translated proteins used in binding reactions. The amount of each DBC-1 derivative retained by GST-ERα (% bound) was quantified and expressed as a percentage of the total input. Percent (%) bound refers to the average and S.D. of at least three independent experiments. Asterisks denote statistically significant ($p<0.05$) binding values relative to GST alone. Note that DBC-1 binds primarily to GST-ERα derivatives 1-595 (full-length ERα) and 302-595 (ERα hormone-binding domain), while GST-ERα binds primarily to DBC-1 derivative 1-150 (N-terminus). Schematic diagrams of ERα and DBC-1 indicate fragments used in binding reactions. Abbreviations used are AF-1, activation function 1; DBD, DNA-binding domain; AF-2/HBD, activation function 2/hormone-binding domain; NLS, putative nuclear localization sequence; LZip, putative leucine zipper.
Figure 3B:
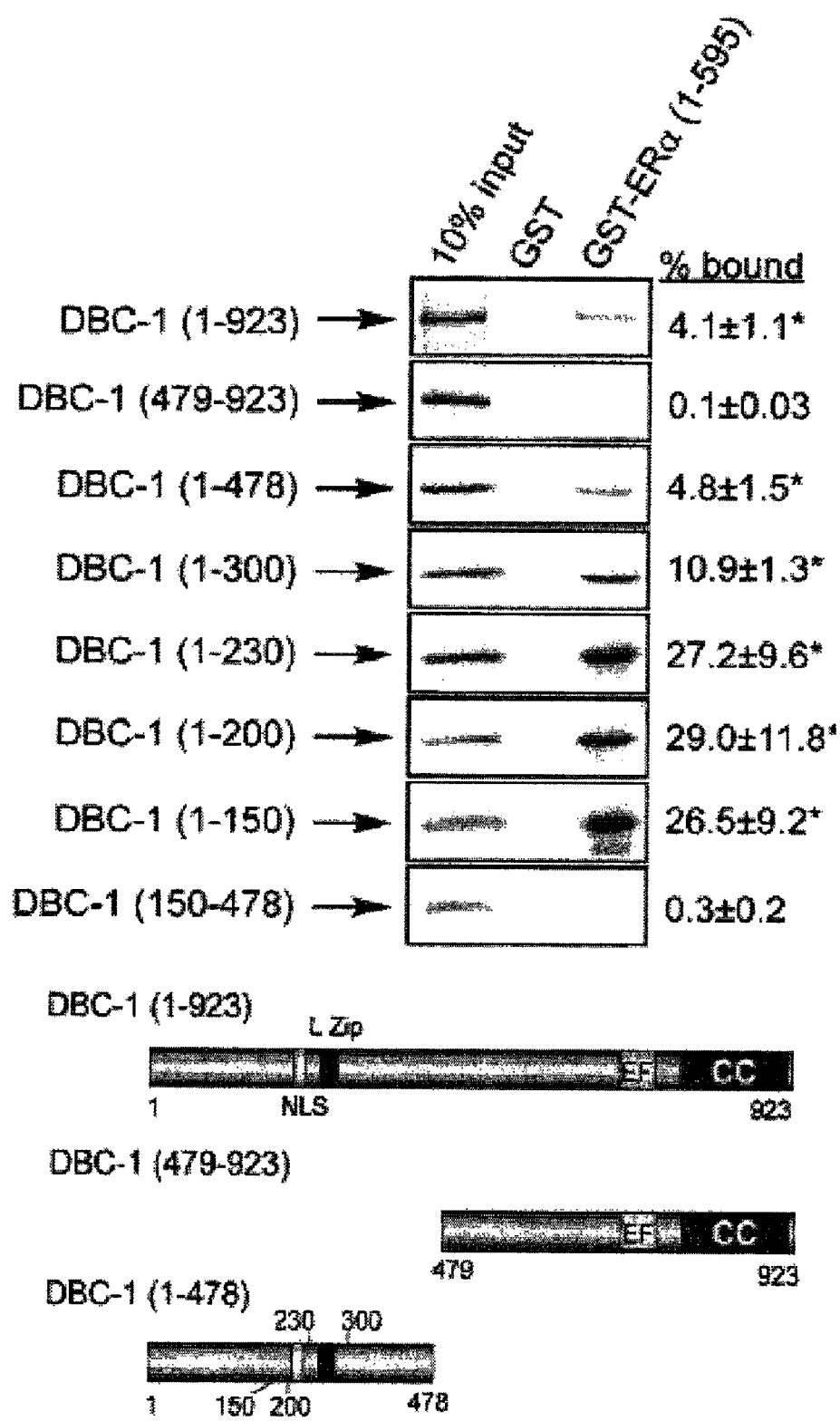

The DBC-1 N-terminus Interacts Directly with the ERα Hormone-Binding Domain in vitro. To determine if DBC-1 interacts directly with unliganded ERα, and to map the reciprocal binding domains on each protein, the ability of GST-ERα derivatives to bind to full-length DBC-1 or DBC-1 truncation fragments produced by in vitro translation were tested. DBC-1 bound most efficiently to GST-ERA derivatives 1-595 (full-length ERα) and 302-595 (ERα hormone-binding domain) (FIG. 3A). Reciprocally, GST-ERα 1-595 (full-length ERα) bound to the extreme amino-terminus of DBC-1 (amino acids 1-150) (FIG. 3B). Thus, in the absence of ligand, the ERα hormone-binding domain can accommodate the DBC-1 amino terminus.

Figure 4A:
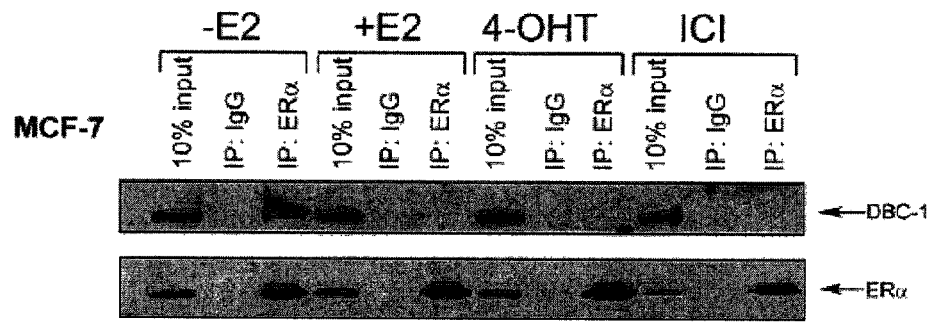
FIGS. 4A and 4B show that tamoxifen and ICI 182,780 disrupt the interaction between DBC-1 and ERα. MCF-7 (FIG. 4A) or BG-1 (FIG. 4B) cells cultured in hormone-free medium for three days were treated with vehicle (−E2), 17-β-estradiol ($10^{-7}$ M; +E2), 4-hydroxytamoxifen ($10^{-6}$ M; 4-OHT), or ICI 182,780 ($10^{-7}$ M; ICI) for one hour prior to cell harvest and immunoprecipitation of whole cell lysates with antibodies specific for ERα. Immunoprecipitates were resolved by SDS-7.5%-PAGE and processed for immunoblot analysis with antibodies specific for DBC-1 or ERα as indicated by arrows. Results are representative of at least three independent experiments.
Figure 4B:
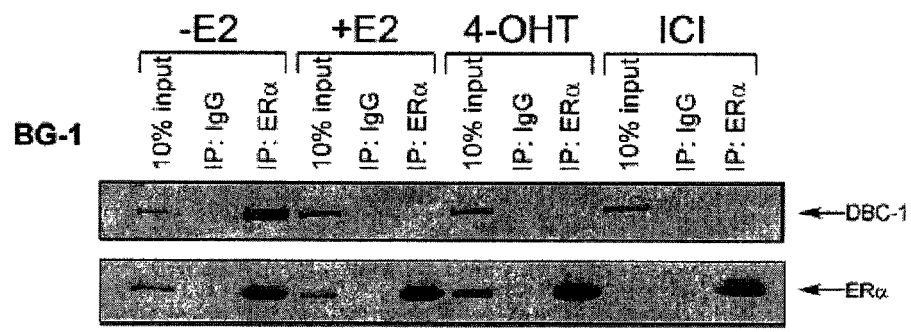

The DBC-1/ERα interface is a novel target of antiestrogens. Antiestrogens are currently the most widely administered endocrine agents for the management of ERα-expressing breast cancers. Antiestrogens competitively displace E2 from the ERα hormone-binding domain and either block ERα function or induce destabilization and degradation of ERα. Tamoxifen, a prototype of the former class, is a selective estrogen receptor modulator (SERM) with antiestrogenic properties in breast, and the most widely administered antiestrogen in breast cancer therapy. Among the latter class of antiestrogens, ICI 182,780 (FASLODEX® (fulvestrant), Astrazeneca, Wilmington, Del.) is a selective estrogen receptor downregulator (SERD) and an effective therapeutic agent used to treat breast cancers that have progressed on prior tamoxifen therapy. Because these compounds bind directly to the ERα hormone-binding domain, the influence of each agent was examined on the DBC-1/ERα interaction. The ability of ERα-specific antibodies to co-immunoprecipitate endogenous DBC-1 was tested in MCF-7 and BG-1 cells cultured in the absence or presence of E2, tamoxifen, or ICI 182,780. Like E2, both tamoxifen and ICI 182,780 disrupted the DBC-1/ERα interaction (FIGS. 4A and 4B).

Figure 5A:
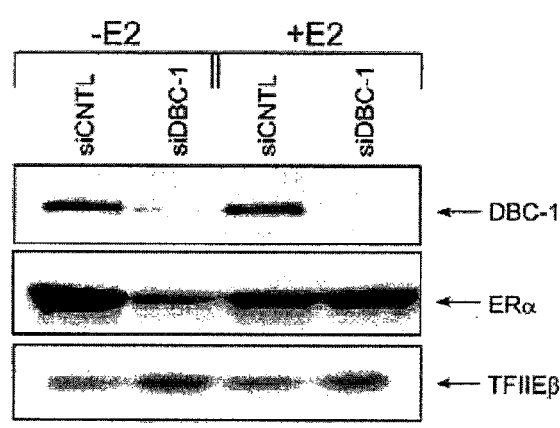
FIGS. 5A and 5B show that RNAi-mediated DBC-1 suppression is accompanied by reduced steady-state levels of unliganded ERα. MCF-7 cells cultured in hormone-free medium for three days were electroporated with control (siCNTL) or DBC-1-specific (siDBC-1) siRNA (21 nM) as indicated. Electroporated cells were cultured without (−E2) or with (+E2) 17-β-estradiol ($10^{-7}$ M) for an additional three days prior to cell harvest. For FIG. 5A, harvested whole cell lysates were resolved by SDS-10%-PAGE and processed by immunoblot analysis with antibodies specific for DBC-1, ERα, or TFIIEβ as indicated by arrows. Results are representative of at least three independent experiments. For FIG. 5B, top panel, immune signals were quantified using a Kodak ImageStation 2000R. ERα protein levels were normalized to TFIIEβ and plotted relative to the ERα protein level in control siRNA cells cultured in the absence of E2, which was arbitrarily assigned a value of 1. Error bars represent the S.D. from the average of at least three independent experiments. For FIG. 5B, bottom panel, RNA was processed by quantitative RT-PCR analysis for the levels of DBC-1, ERα, and GAPDH mRNAs. ERα RNA levels were normalized to GAPDH levels, and expressed relative to the level of ERα RNA in control siRNA cells cultured in the absence of E2, which was arbitrarily assigned a value of 1. Error bars represent the S.D. from the average of at least three independent experiments performed in duplicate.
Figure 5B:
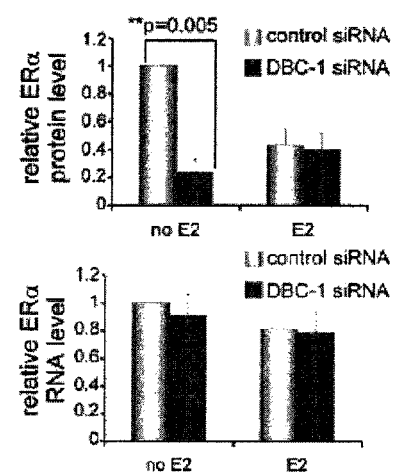

DBC-1 is an ERα-dependent prosurvival factor in breast cancer cells. To examine the biological consequence of the DBC-1/ERα interaction in human breast cancer cells, conditions for RNAi-mediated DBC-1 depletion was established in MCF-7 cells. RNAi-mediated DBC-1 knockdown was accompanied by a significant reduction in the steady-state level of ERα protein, but not ERα mRNA, suggesting that DBC-1 modulates ERα protein synthesis or stability (FIG. 5). Notably, DBC-1 knockdown preferentially reduced the steady-state level of unliganded, but not liganded, ERα protein. Therefore, DBC-1 stabilizes unliganded ERα by virtue of their direct physical association (FIG. 5).

Figure 6:
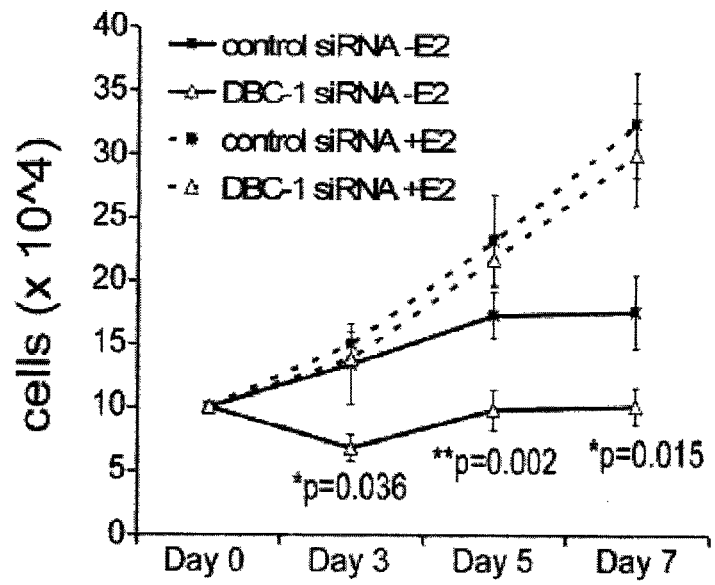
FIG. 6 shows RNAi-mediated DBC-1 depletion inhibits estrogen-independent proliferation in human breast cancer cells. MCF-7 cells cultured in hormone-free medium for three days were electroporated with control or DBC-1-specific siRNA (21 nM) as indicated and cultured without (−E2) or with (+E2) 17-β-estradiol ($10^{-7}$ M). Culture medium was replaced every two days. Cell proliferation was monitored by counting with trypan blue exclusion for seven days following electroporation. p-values are in comparison to controls. Error bars represent the S.D. from the average of at least three independent experiments performed in triplicate.

Because DBC-1 is a direct binding partner and key determinant of steady-state ERα protein levels, its role in ERα-dependent breast cancer cell proliferation and survival was examined. RNAi-mediated DBC-1 depletion significantly reduced E2-independent, but not E2-dependent, MCF-7 cell proliferation, an observation concordant with the fact that DBC-1 preferentially binds to and modulates the levels of unliganded ERα (FIG. 6). Transient DBC-1 knockdown cells experienced an initial (~2-fold) reduction in cell number on day 3 after siRNA delivery followed by growth kinetics similar to control siRNA knockdown cells. To determine whether DBC-1 knockdown causes an increase in apoptotic cell death, the influence of DBC-1 knockdown on the apoptotic fate of MCF-7 cells cultured in the absence of E2 was examined.

Figures 7A, 7B:
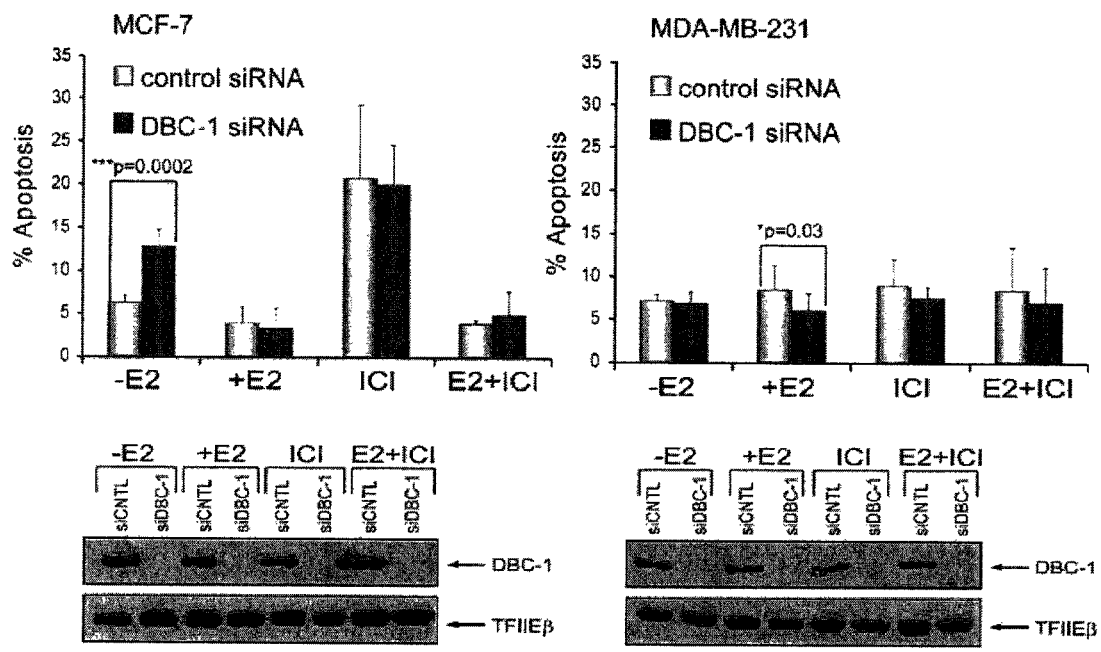
FIGS. 7A and 7B show that DBC-1 is an ERα-dependent prosurvival factor in human breast cancer cells. MCF-7 (FIG. 7A) or MDA-MB-231 (FIG. 7B) cells cultured in hormone-free medium for three days were electroporated with control or DBC-1-specific siRNA (21 nM) as indicated. Forty-eight hours following electroporation, cells were treated with vehicle (−E2), 17-β-estradiol ($10^{-7}$ M; +E2), ICI 182,780 ($10^{-7}$ M; ICI), or a combination of E2 and ICI 182,780 (E2+ICI) for an additional twenty-four hours prior to cell harvest. For FIGS. 7A and 7B, Top panels, harvested cells were stained with Annexin V-FITC and propidium iodide prior to quantification of apoptosis by flow cytometric analyses. p-values are in comparison to controls. Error bars represent the S.D. from the average of at least three independent experiments performed in triplicate. For FIGS. 7A and 7B, Bottom panels, cell lysates from representative apoptosis assays in panels (FIG. 7A) and (FIG. 7B) were resolved by SDS-10%-PAGE and processed by immunoblot analysis with the indicated antibodies specific for DBC-1 or TFIIEβ as a loading control.

Under these conditions, DBC-1 depletion increased the percentage of apoptotic cells from 6.2% to 12.8%, thus revealing an anti-apoptotic function for DBC-1 in the absence of hormone (FIG. 7A). To determine if DBC-1 promotes hormone-independent cell survival through its direct interaction with ERα, the influence of DBC-1 knockdown on the apoptotic fate of MCF-7 cells cultured in the presence of E2, which disrupts the DBC-1/ERα interaction, or ICI 182,780, which not only disrupts the DBC-1/ERα interaction but also drastically depletes ERα protein levels, was examined. Notably, DBC-1 depletion had no effect on MCF-7 cell apoptosis in the presence of either E2 or ICI 182,780 (FIG. 7A). Furthermore, DBC-1 depletion did not enhance apoptosis of ERα-negative MDAMB-231 breast cancer cells cultured in the absence of E2 (FIG. 7B). Taken together, these observations show that DBC-1 functions to promote E2-independent breast cancer cell survival in an ERα-dependent manner.

Example 2

DBC-1 and ERα are Expressed in Primary Human Breast Carcinomas

Figures 9A, 9B, 9C, 9D, 9E, 9F, 9G, 9H, 9I, 9J, 9K, 9L:
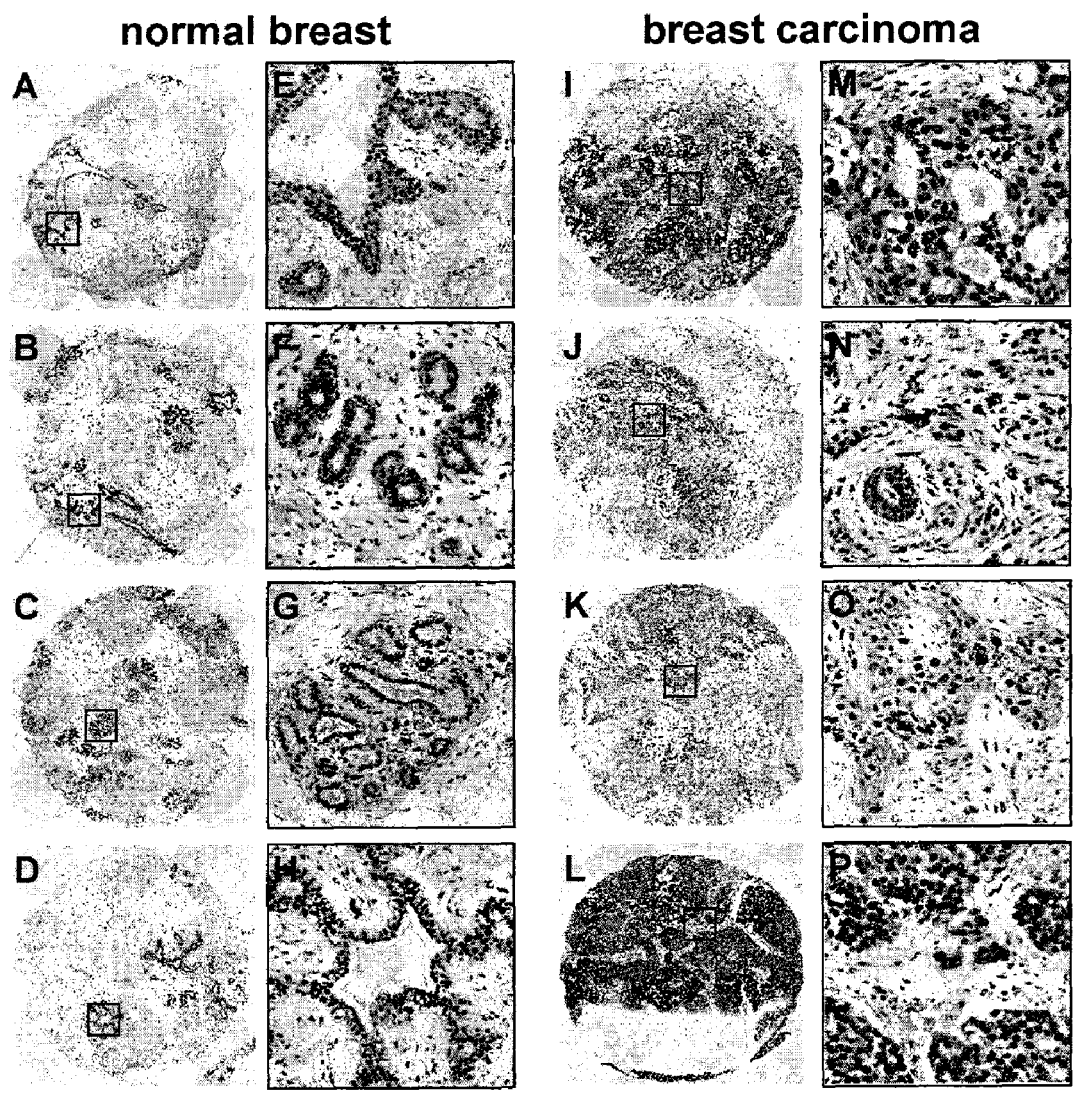
FIGS. 9A-9L are pictures of representative immunohistochemical staining of DBC-1 in normal and cancerous breast tissues. (A-D) DBC-1 staining in normal breast tissue. (E-H) Enlarged images of (A-D), respectively. (I-L) DBC-1 staining in invasive breast cancer. (M-P) enlarged images of (I-L), respectively.

Consistent with the results above showing that DBC-1 modulates ERα expression and survival activity, a strong association between expression levels of DBC-1 and ERα was observed in primary human breast carcinomas (FIG. 9 and Table 1). FIG. 9 shows pictures of representative immunohistochemical staining of DBC-1 in normal and cancerous breast tissues. FIG. 9 shows pictures of representative immunohistochemical staining of DBC-1 in normal and cancerous breast tissues. For Table 1, DBC-1, ERα, and PR protein levels were examined by immunohistochemistry in 88 breast tumor samples derived from the San Antonio Cancer Institute tissue bank (27 samples) and the Cooperative Human Tissue Network and the Tissue Array Research Program (TARP) of the National Cancer Institute (TARP Breast and Ovarian Cancer Array) (61 samples). Tissue microarrays were deparaffinized and rehydrated prior to immunostaining using antibodies specific for ERα (ER 6F11, Novocastra/Vison BioSystems, Inc., Norwell, Mass.), PR (PR 636, DAKO, Carpinteria, Calif.), or DBC-1 (mouse polyclonal antibody against DBC-1 amino acids 475-923). Stained microarrays were scanned into a Scanscope CS scanner system (Aperio Technologies, Vista, Calif.) and images were analyzed using the nuclear IHC algorithm bundled with the Aperio TMALab software (Aperio Technologies, Vista, Calif.). The relationships among staining percentages for each protein were compared using Spearman's rank order correlation coefficient analysis. Statistical tests were two-sided. Table 1 shows that DBC-1, ERα, and progesterone receptor (PR) protein levels were all significantly positively correlated in primary human breast carcinomas.

TABLE 1

DBC-1, ERα, and progesterone receptor (PR) protein levels in primary human breast carcinomas.

|  | ERα | PgR | DBC-1 |
|---|---|---|---|
| PgR | $p < 0.001$ $(R = 0.83)^a$ | 1 |  |
| DBC-1 | $p < 0.001$ $(R = 0.52)$ | $p < 0.001$ $(R = 0.64)$ | 1 |

$^a$Values in parentheses are Spearman rank correlation coefficients. Comparisons wherein $p < 0.05$ are statistically significant.

Together, these findings establish a principal biological function for DBC-1 in the modulation of ERα expression and hormone-independent breast cancer cell survival.

Example 3

Figure 10A:
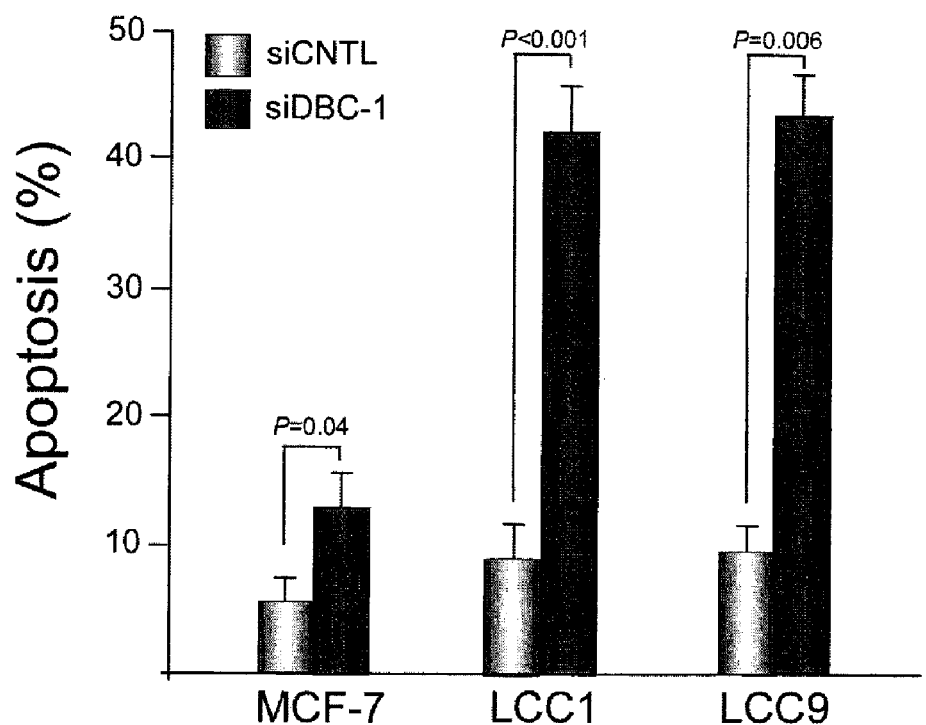
FIGS. 10A and 10B show that DBC-1 is required for endocrine resistant breast cancer cell survival. MCF-7, LCC1, and LCC9 cells cultured in hormone-free medium were electroporated with control (siCNTL) or DBC-1-specific (siDBC-1) siRNAs (21 nM) as indicated seventy-two hours prior to harvest.
Figure 10B:
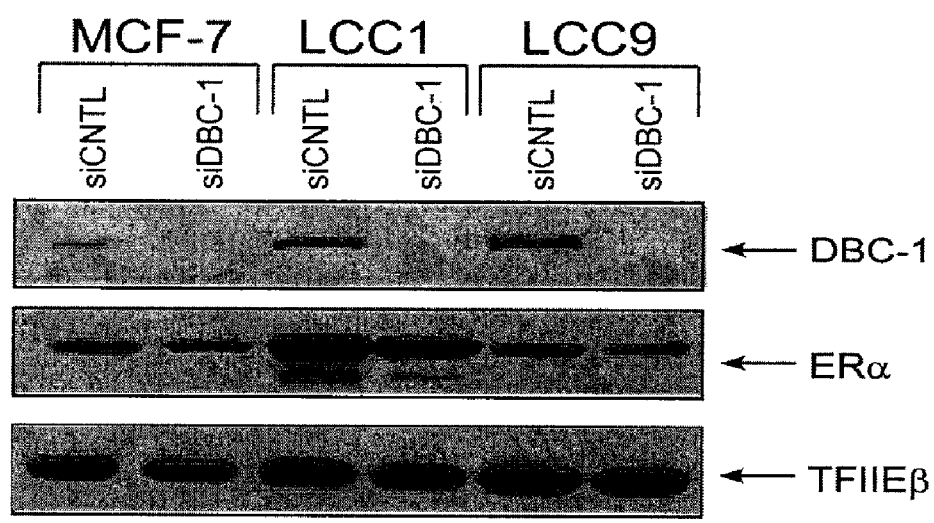
Figure 11A:
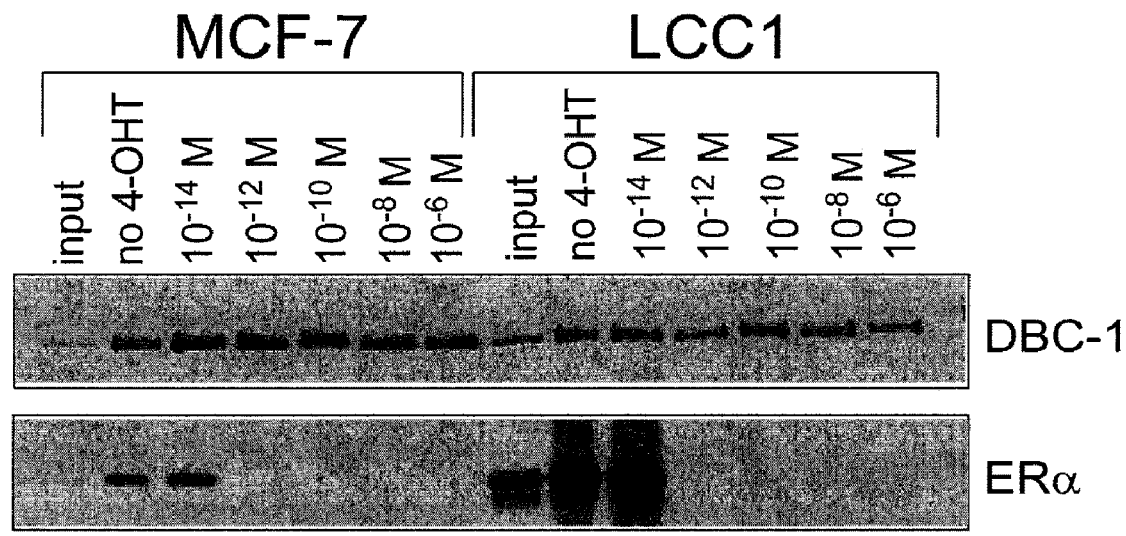
FIGS. 11A and 11B show that the DBC-1/ERα complex is resistant to tamoxifen-mediated disruption in tamoxifen-resistant LCC9 cells. MCF-7, LCC1, or LCC9 cells cultured in hormone-free medium were treated with increasing concentrations of 4-hydroxytamoxifen (4-OHT) as indicated for one hour prior to cell harvest and immunoprecipitation of whole cell lysates with antibodies specific for DBC-1. Immunoprecipitates were resolved by SDS-7.5%-PAGE and processed for immunoblot analysis with antibodies specific for DBC-1 or ERα as indicated.
Figure 11B:
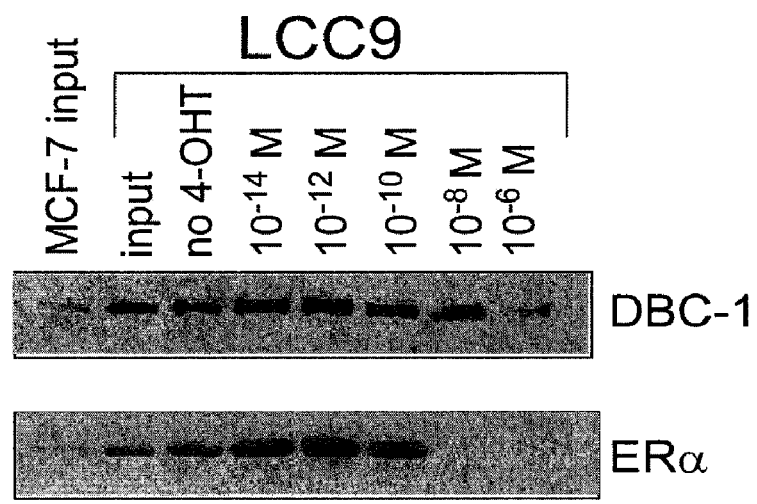

DBC-1 is Required for Endocrine Resistant Breast Cancer Cell Survival and the DBC-1/ERα Complex is Resistant to Tamoxifen-Mediated Disruption in Tamoxifen-Resistant Cells Since DBC-1 is a hormone-independent prosurvival factor in human breast cancer cells, its role in endocrine resistance was examined. The expression and function of DBC-1 was examined in a three-stage MCF-7 cell-based model of acquired endocrine resistant breast cancer (Bouker et al., 2004, Cancer Res 64:4030-9; Brunner et al., 1997, Cancer Res 57:3486-93; and Clarke et al., 1989, Proc Natl Acad Sci USA 86:3649-53). This model system is based on the ERα-positive MCF-7 human breast cancer cell line, which is estrogen-dependent for growth and sensitive to the growth inhibitory actions of antiestrogens, including the selective estrogen receptor modulator (SERM) tamoxifen and the selective estrogen receptor downregulator (SERD) ICI 182,780 (faslodex, fulvestrant). Long-term passage of MCF-7 tumor xenografts in ovariectomized mice led to derivation of the MCF-7/LCC1 (LCC1) cell line, which is estrogen-independent but antiestrogen-sensitive (Clarke et al., 1989, Proc Natl Acad Sci USA 86:3649-53). Subsequent long-term culture of LCC1 cells in vitro in the presence of ICI 182,780 produced the MCF7/LCC9 (LCC9) cell line, which is fully resistant to both estrogen and ICI 182,780, and cross-resistant to tamoxifen (Brunner et al., 1997, Cancer Res 57:3486-93). This model system, derived through stepwise selection of MCF-7 cells first to a low estrogen environment in vivo followed by long-term culture in the presence of an antiestrogen, mimics a clinical scenario [Phase II endocrine resistance (Jordan et al., 2005, Breast 14:624-30)] in which breast cancer patients undergo exhaustive hormonal therapy (first-line treatment with an aromatase inhibitor followed by second-line treatment with an antiestrogen) leading to the acquisition of a fully estrogen-independent and antiestrogen-resistant tumor phenotype. Using this three-stage MCF-7 cell-based model of acquired endocrine resistant breast cancer, it was determined that DBC-1 is upregulated during the acquisition of endocrine resistance and, further, that targeted suppression of DBC-1 triggers a rapid and profound apoptotic response in endocrine resistant LCC1 and LCC9 breast cancer cells (FIG. 10). It was also observed that a direct correlation exists between antiestrogen resistance and DBC-1/ERα complex formation in this model system. The DBC-1/ERα complex in tamoxifen-sensitive MCF-7 and LCC1 cells is disrupted by tamoxifen at a concentration ($10^{-12}$ M), four orders of magnitude lower than that required to disrupt the DBC-1/ERα complex in tamoxifen-resistant LCC9 cells ($10^{-8}$ M) (FIG. 11). These data show that a direct correlation exists between tamoxifen resistant breast cancer cell growth and DBC-1/ERα complex formation. These data also show that the DBC-1/ERα complex drives antiestrogen resistance through a pro-survival pathway.

What is claimed is:

1. A method of determining whether a cancer cell is sensitive to endocrine therapy comprising:
   a) obtaining a population of cancer cells; and
   b) determining the presence of binding of DBC-1 and Estrogen Receptor α (ERα), the presence of binding of DBC-1 and ERα as compared to a control indicating that the cancer cells are not sensitive to endocrine therapy.

2. A method of determining whether a subject with cancer is suitable for treatment with endocrine therapy comprising:
   a) obtaining a biological sample comprising cancer cells from the subject; and
   b) determining the presence of binding of DBC-1 and ERα, the presence of binding of DBC-1 and ERα as compared to a control indicating that the subject is not suitable for treatment with endocrine therapy.

3. The method of claim 2, wherein the cancer cells are endometrial cancer cells, breast cancer cells, ovarian cancer cells or prostate cancer cells.

4. The method of claim 2, wherein step b) is carried out using a polyclonal antibody that binds DBC-1 in the region of amino acids 475-923.

5. A method of determining a susceptibility to hormone resistant cancer in a subject comprising:
   a) obtaining a biological sample comprising cancer cells from the subject; and
   b) determining the presence of binding of DBC-1 and ER-α, wherein the presence of binding of DBC-1 and ER-α as compared to a control indicates that the subject is susceptible to hormone resistant cancer.

6. The method of claim 5, wherein the subject has endometrial cancer, breast cancer, ovarian cancer or prostate cancer.

7. The method of claim 5, wherein step b) is carried out using a polyclonal antibody that binds DBC-1 in the region of amino acids 475-923.

* * * * *

UNITED STATES PATENT AND TRADEMARK OFFICE
CERTIFICATE OF CORRECTION

PATENT NO. : 7,807,383 B2  Page 1 of 1
APPLICATION NO. : 12/104709
DATED : October 5, 2010
INVENTOR(S) : Thomas G. Boyer et al.

It is certified that error appears in the above-identified patent and that said Letters Patent is hereby corrected as shown below:

Add the following claims:

Col. 30, claim 8.   The method of claim 1, wherein the cancer cells are endometrial cancer cells, breast cancer cells, ovarian cancer cells or prostate cancer cells.

Col. 30, claim 9.   The method of claim 1, wherein step b) is carried out using a polyclonal antibody that binds DBC-1 in the region of amino acids 475-923.

Signed and Sealed this
Eighteenth Day of January, 2011

David J. Kappos
*Director of the United States Patent and Trademark Office*

UNITED STATES PATENT AND TRADEMARK OFFICE
CERTIFICATE OF CORRECTION

PATENT NO.         : 7,807,383 B2
APPLICATION NO.    : 12/104709
DATED              : October 5, 2010
INVENTOR(S)        : Thomas G. Boyer et al.

It is certified that error appears in the above-identified patent and that said Letters Patent is hereby corrected as shown below:

Delete the Title page and substitute therefore the attached Title page showing corrected number of claims in patent.

Column 30, at line 33,
Add the following claims:

8.     The method of claim 1, wherein the cancer cells are endometrial cancer cells, breast cancer cells, ovarian cancer cells or prostate cancer cells.

9.     The method of claim 1, wherein step b) is carried out using a polyclonal antibody that binds DBC-1 in the region of amino acids 475-923.

This certificate supersedes the Certificate of Correction issued January 18, 2011.

Signed and Sealed this
Fifteenth Day of February, 2011

David J. Kappos
*Director of the United States Patent and Trademark Office*

(12) United States Patent
Boyer et al.

(10) Patent No.: US 7,807,383 B2
(45) Date of Patent: Oct. 5, 2010

(54) DIAGNOSING AND TREATING HORMONE RESISTANT CANCERS

(75) Inventors: Thomas G. Boyer, San Antonio, TX (US); Amy M. Trauernicht, Chula Vista, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/104,709

(22) Filed: Apr. 17, 2008

(65) Prior Publication Data
US 2009/0062179 A1 Mar. 5, 2009

Related U.S. Application Data

(60) Provisional application No. 60/912,752, filed on Apr. 19, 2007.

(51) Int. Cl.
*G01N 33/48* (2006.01)
*G01N 33/53* (2006.01)
*G01N 33/567* (2006.01)

(52) U.S. Cl. .......... 435/7.1; 435/7.8; 436/63; 436/64; 436/503; 436/811

(58) Field of Classification Search .......... None
See application file for complete search history.

(56) References Cited

OTHER PUBLICATIONS

Tolcher et al (Clinical Cancer Research, 2002, vol. 8, pp. 2530-2535).*
Cripps et al (Clinical Cancer Research, 2002, 8, pp. 2188-2192).*
James and Gibson (Blood, 1998, vol. 91, pp. 371-382).*
Extended Medline abstract of Mangala et al, Methods in Mol. Biol. 2009.*
Extended Medline abstract of Koldenhoff et al, Methods in Mol Bio, 2009.*
Merkel et al, Mol Pharmaceutics, 2009, vol. 8, pp. 1246-1280.*
Song et al, Exp Mol Med, 2007, vol. 39, pp. 722-732.*
Difeo et al, Cancer Research, 2009, vol. 69, pp. 4733-4741.*
He et al, Cancer biotherapy and Radiopharm, 2009, vol. 24, pp. 249-259.*
Jain (Science, 1996, vol. 271, pp. 1079-1080).*
Tarahula et al, Journal of controlled Release, 2009, vol. 140, pp. 284-293.*
Ali and Coombes. 2000. Estrogen receptor alpha in human breast cancer: occurrence and significance. J Mammary Gland Biol Neoplasia 5:271-81.
Bagatell et al. 2001. Destabilization of steroid receptors by heat shock protein 90-binding drugs: a ligand-independent approach to hormonal therapy of breast cancer. Clin Cancer Res 7:2076-84.
Beausoleil et al. 2004. Large-scale characterization of HeLa cell nuclear phosphoproteins. Proc Natl Acad Sci U S A 101: 12130-5.
Bhat-Nakshatri et al. 2002. Identification of signal transduction pathways involved in constitutive NF-kappaB activation in breast cancer cells. Oncogene 21:2066-78.
Bittner. 2005. A window on the dynamics of biological switches. Nat Biotechnol 23:183-4.

Bouker et al. 2004. Interferon regulatory factor-1 mediates the proapoptotic but not cell cycle arrest effects of the steroidal antiestrogen ICI 182,780 (faslodex, fulvestrant) Cancer Res. 64:4030-9.
Bouwmeester et al. 2004. A physical and functional map of the human TNF-alpha/NF-kappa B signal transduction pathway. Nat Cell Biol 6:97-105.
Brunner et al. 1997 MCF7/LCC9: an antiestrogen-resistant MCF-7 variant in which acquired resistance to the steroidal antiestrogen ICI 182,780 confers an early cross-resistance to the nonsteroidal antiestrogen tamoxifen Cancer Res. 57:3486-93.
Clarke et al. 2004. Steroid receptors in human breast cancer. Trends Endocrinol Metab 15:316-23.
Clarke et al. 1989. Progression of human breast cancer cells from hormone-dependent to hormone-independent growth both in vitro and in vivo. Proc Natl Acad Sci U S A 86:3649-53.
Colditz et al. 2004. Risk factors for breast cancer according to estrogen and progesterone receptor status. J Natl Cancer Inst 96:218-28.
Couse and Korach. 1999. Estrogen receptor null mice: what have we learned and where will they lead us? Endocr Rev 20:358-417.
deGraffenried et al. 2004. NF-kappa B inhibition markedly enhances sensitivity of resistant breast cancer tumor cells to tamoxifen Ann Oncol 15:885-90.
Dowsett et al. 1999. Clinical studies of apoptosis and proliferation in breast cancer. Endocr Relat Cancer 6:25-8.
Fanelli et al. 1996. Estrogen receptors, progesterone receptors, and cell proliferation in human breast cancer. Breast Cancer Res Treat 37:217-28.
Fliss et al. 2000. Control of estrogen receptor ligand binding by Hsp90. J Steroid Biochem Mol Biol 72:223-30.
Hamaguchi et al. 2002. DBC2, a candidate for a tumor suppressor gene involved in breast cancer. Proc Natl Acad Sci U S A 99:13647-52.
Hilakivi-Clarke et al. 2002. Dietary modulation of pregnancy estrogen levels and breast cancer risk among female rat offspring. Clin Cancer Res 8:3601-10.
Howell. 2006. Pure oestrogen antagonists for the treatment of advanced breast cancer. Endocr Relat Cancer 13:689-706.
Huang et al. 2005. Molecular basis of therapeutic strategies for breast cancer. Curr Drug Targets Immune Endocr Metabol Disord 5:379-96.
Ignar-Trowbridge et al. 1993. Peptide growth factors elicit estrogen receptor-dependent transcriptional activation of an estrogen-responsive element. Mol Endocrinol 7:992-8.
Jordan. 2004. Selective estrogen receptor modulation: concept and consequences in cancer. Cancer Cell 5:207-13.
Key et al. 2001. Epidemiology of breast cancer. Lancet Oncol 2:133-40.
Koibuchi et al. 1999. The mechanisms of antitumor effects of luteinizing hormone releasing hormone agonist (buserelin) in 7,12-dimethylbenz(a)anthracene-induced rat mammary cancer. Int J Mol Med 4 145-8
Lee et al. 2002. Radicicol represses the transcriptional function of the estrogen receptor by suppressing the stabilization of the receptor by heat shock protein 90. Mol Cell Endocrinol 188:47-54
Liao et al. 1998. Promotion of estrogen-induced mammary gland carcinogenesis by androgen in the male Noble rat: probable mediation by steroid receptors. Carcinogenesis 19:2173-80.
Liu and Picard. 1998. Bioactive steroids as contaminants of the common carbon source galactose. FEMS Microbiol Lett 159:167-71

(Continued)

*Primary Examiner* — Karen A Canella
(74) *Attorney, Agent, or Firm* — Fish & Richardson P.C.

(57) ABSTRACT

Provided herein are methods and compositions related to diagnosing and treating hormone resistant cancers.

9 Claims, 10 Drawing Sheets

SEQUENCE LISTING

<160> NUMBER OF SEQ ID NOS: 14

<210> SEQ ID NO 1
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 1
caacuggugu ggcuacuugu u                                                 21

<210> SEQ ID NO 2
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 2
caaguagcca caccaguugu u                                                 21

<210> SEQ ID NO 3
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 3
cuacugagcc uuccugaaau u                                                 21

<210> SEQ ID NO 4
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 4
uuucaggaag gcucaguagu u                                                 21

<210> SEQ ID NO 5
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 5
cagcuugcau gacuacuuuu u                                                 21

<210> SEQ ID NO 6
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 6
aaaguaguca ugcaagcugu u                                                 21

<210> SEQ ID NO 7
<211> LENGTH: 21

```
<212> TYPE: RNA
<213> ORGANISM: Artificial Sequence
<220> FEATURE:
<223> OTHER INFORMATION: Synthetically generated oligonucleotide

<400> SEQUENCE: 7
cagcgggucu ucacugguau u                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 8
uaccagugaa gacccgcugu u                                              21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
atgtcccagt ttaagcgcca g                                              21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
caaccccaaa gtagtcatgc aa                                             22

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccaccaacca gtgcaccatt                                                20

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggtcttttcg tatcccacct ttc                                            23

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
```

```
cctgttcgac agtcagccg                                                    19

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cgaccaaatc cgttgactcc                                                   20
```